US009655808B2

(12) United States Patent
Peddicord

(10) Patent No.: US 9,655,808 B2
(45) Date of Patent: *May 23, 2017

(54) URINARY INCONTINENCE DEVICE AND METHOD AND STIMULATION DEVICE AND METHOD

(71) Applicant: INCONTROL MEDICAL, LLC, Brookfield, WI (US)

(72) Inventor: Herschel Peddicord, Longboat Key, FL (US)

(73) Assignee: INCONTROL MEDICAL, LLC, Brookfield, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,555

(22) Filed: Jul. 21, 2014

(65) Prior Publication Data

US 2014/0330178 A1 Nov. 6, 2014

Related U.S. Application Data

(63) Continuation of application No. 13/458,734, filed on Apr. 27, 2012, now Pat. No. 8,784,345, which is a
(Continued)

(51) Int. Cl.
*A61H 19/00* (2006.01)
*A61H 23/02* (2006.01)
(Continued)

(52) U.S. Cl.
CPC ............. *A61H 19/40* (2013.01); *A61H 19/00* (2013.01); *A61H 19/34* (2013.01); *A61H 19/44* (2013.01);
(Continued)

(58) Field of Classification Search
CPC .......... A61H 9/00; A61H 15/00; A61H 19/00; A61H 19/40; A61H 19/44; A61H 19/34;
(Continued)

(56) References Cited

U.S. PATENT DOCUMENTS 3,403,684 A 10/1968 Stiebel et al.
3,800,800 A 4/1974 Garbe et al.
(Continued)

FOREIGN PATENT DOCUMENTS

| KR | 10674042 B1 | 1/2007 |
| KR | 10895220 B1 | 5/2009 |
| WO | WO-2010/067360 A2 | 6/2010 |

OTHER PUBLICATIONS

Extended European Search Report for European Patent Application No. EP 117964389, dated Apr. 16, 2014, 7 pages.
(Continued)

*Primary Examiner* — Justine Yu
*Assistant Examiner* — Colin W Stuart
(74) *Attorney, Agent, or Firm* — Foley & Lardner LLP

(57) ABSTRACT

A method for treating urinary incontinence is provided. The method includes providing a device having an expandable portion having an outer surface, a first electrode, and a second electrode, the first and second electrodes coupled to the outer surface of the expandable portion and configured to cause a contraction of a muscle in communication with the electrodes. The method further includes causing the expandable portion to inflate such that the first and second electrodes contact vaginal walls and causing a contraction of a muscle in communication with the electrode.

20 Claims, 22 Drawing Sheets

Related U.S. Application Data continuation of application No. PCT/US2011/040714, filed on Jun. 16, 2011, and a continuation of application No. 13/739,750, filed on Jan. 11, 2013, now Pat. No. 8,818,512, which is a continuation of application No. 13/458,857, filed on Apr. 27, 2012, now Pat. No. 8,369,953, which is a continuation of application No. PCT/US2011/040714, filed on Jun. 16, 2011.

(60) Provisional application No. 61/355,822, filed on Jun. 17, 2010, provisional application No. 61/430,072, filed on Jan. 5, 2011.

(51) Int. Cl.
  *A61N 1/05* (2006.01)
  *A61N 1/36* (2006.01)
  *A61H 23/00* (2006.01)
  *A61H 9/00* (2006.01)

(52) U.S. Cl.
  CPC ......... *A61H 23/00* (2013.01); *A61H 23/0263* (2013.01); *A61N 1/0524* (2013.01); *A61N 1/36007* (2013.01); *A61H 9/0078* (2013.01); *A61H 2201/0103* (2013.01); *A61H 2201/0153* (2013.01); *A61H 2201/5015* (2013.01); *A61H 2201/5035* (2013.01); *A61H 2201/5046* (2013.01); *A61H 2201/5048* (2013.01); *A61H 2201/5071* (2013.01); *A61H 2201/5097* (2013.01); *A61H 2230/65* (2013.01); *A61H 2230/655* (2013.01)

(58) Field of Classification Search
  CPC ........ A61H 19/50; A61H 21/00; A61H 23/00; A61H 23/02; A61H 23/04; A61H 23/0263
  See application file for complete search history.

(56) References Cited

U.S. PATENT DOCUMENTS

| | | |
|---|---|---|
| 4,106,511 A | 8/1978 | Erlandsson |
| 4,296,760 A | 10/1981 | Carlsson et al. |
| 4,881,526 A | 11/1989 | Johnson et al. |
| 4,909,263 A | 3/1990 | Norris |
| 4,969,474 A | 11/1990 | Schwarz |
| 5,010,895 A | 4/1991 | Maurer et al. |
| D320,087 S | 9/1991 | Sholzberg et al. |
| 5,199,443 A | 4/1993 | Maurer et al. |
| 5,314,465 A | 5/1994 | Maurer et al. |
| 5,370,671 A | 12/1994 | Maurer et al. |
| 5,376,064 A | 12/1994 | Cerny |
| 5,385,577 A | 1/1995 | Maurer et al. |
| 5,562,717 A | 10/1996 | Tippey et al. |
| 5,662,699 A | 9/1997 | Hamedi et al. |
| 5,702,428 A | 12/1997 | Tippey et al. |
| 5,800,501 A | 9/1998 | Sherlock |
| 5,875,778 A | 3/1999 | Vroegop |
| 5,881,731 A | 3/1999 | Remes |
| 6,139,569 A | 10/2000 | Ingle et al. |
| 6,190,307 B1 | 2/2001 | Tsai |
| 6,289,894 B1 | 9/2001 | Remes |
| 6,488,673 B1 | 12/2002 | Laufer et al. |
| 6,625,495 B1 | 9/2003 | Alon et al. |
| 6,741,895 B1 | 5/2004 | Gafni et al. |
| 6,905,471 B2 | 6/2005 | Leivseth et al. |
| 7,079,882 B1 | 7/2006 | Schmidt |
| 7,104,950 B2 | 9/2006 | Levy |
| D536,097 S | 1/2007 | Nan |
| D536,797 S | 2/2007 | Klearman et al. |
| D546,964 S | 7/2007 | Wu |
| 7,341,566 B2 | 3/2008 | Nan |
| 7,438,681 B2 | 10/2008 | Kobashikawa et al. |
| D592,758 S | 5/2009 | Kain |
| 7,534,203 B2 | 5/2009 | Gil |
| 7,577,476 B2 | 8/2009 | Hochman et al. |
| D603,523 S | 11/2009 | Nan et al. |
| D606,206 S | 12/2009 | Nan et al. |
| D606,207 S | 12/2009 | Nan et al. |
| D606,208 S | 12/2009 | Nan et al. |
| D615,663 S | 5/2010 | Nan |
| 7,845,985 B2 | 12/2010 | Brunker et al. |
| 7,931,605 B2 | 4/2011 | Murison |
| 7,957,794 B2 | 6/2011 | Hochman et al. |
| 7,998,057 B2 | 8/2011 | Kain |
| 8,369,953 B2 | 2/2013 | Peddicord |
| 8,509,900 B2 | 8/2013 | Boyd et al. |
| 8,784,345 B2 * | 7/2014 | Peddicord ............ A61H 9/0078 601/15 |
| 8,818,512 B2 * | 8/2014 | Peddicord ............ A61H 9/0078 607/104 |
| 2003/0083590 A1 | 5/2003 | Hochman et al. |
| 2004/0030360 A1 | 2/2004 | Eini et al. |
| 2004/0054392 A1 | 3/2004 | Dijkman |
| 2004/0082859 A1 | 4/2004 | Schaer |
| 2007/0118058 A1 | 5/2007 | Isshiki |
| 2007/0185417 A1 | 8/2007 | Mittal et al. |
| 2008/0009775 A1 | 1/2008 | Murison |
| 2008/0103519 A1 | 5/2008 | Bonutti |
| 2009/0069730 A1 | 3/2009 | Knyrim |
| 2009/0093673 A1 | 4/2009 | Lee |
| 2009/0171144 A1 | 7/2009 | Squicciarini |
| 2009/0177029 A1 | 7/2009 | Alilovich |
| 2009/0222058 A1 | 9/2009 | Craggs |
| 2009/0222060 A1 | 9/2009 | Boyd et al. |
| 2009/0228064 A1 | 9/2009 | Boyd et al. |
| 2009/0228067 A1 | 9/2009 | Boyd et al. |
| 2009/0270963 A1 | 10/2009 | Pelger et al. |
| 2009/0275796 A1 | 11/2009 | Gil |
| 2009/0281397 A1 | 11/2009 | Lavoisier |
| 2010/0004707 A1 | 1/2010 | Hochman et al. |
| 2010/0041944 A1 | 2/2010 | Levy |
| 2010/0087757 A1 * | 4/2010 | Hoffman ............... A61B 5/0002 600/591 |
| 2010/0106216 A1 | 4/2010 | Cha et al. |
| 2010/0174136 A1 | 7/2010 | Shim |
| 2010/0174137 A1 | 7/2010 | Shim |
| 2010/0174213 A1 | 7/2010 | Shim |
| 2010/0174218 A1 | 7/2010 | Shim |
| 2011/0230931 A1 | 9/2011 | Hagege |
| 2012/0215141 A1 | 8/2012 | Peddicord |
| 2012/0215280 A1 | 8/2012 | Peddicord |
| 2012/0265044 A1 | 10/2012 | Broens |
| 2013/0261702 A1 | 10/2013 | Garfield et al. |
| 2014/0200646 A1 | 7/2014 | Boyd et al. |

OTHER PUBLICATIONS

International Search Report and Written Opinion for Application No. PCT/US2011/040714, mail date Feb. 17, 2012, 9 pages.
Notice of Allowance for U.S. Appl. No. 13/458,857, mail date Sep. 28, 2012, 9 pages.
Office Action for U.S. Appl. No. 13/458,734 Dated Dec. 5, 2013, 23 pages.
Office Action for U.S. Appl. No. 13/458,734, mail date May 7, 2013, 22 pages.
Office Action for U.S. Appl. No. 13/458,857, mail date Jul. 3, 2012, 6 pages.
Office Action for U.S. Appl. No. 13/739,750 Dated Jan. 9, 2014, 10 pages.
Office Action for U.S. Appl. No. 13/739,750, mail date Aug. 1, 2013, 9 pages.
Patent Examination Report No. 1 for Australian Patent Application No. 2011268245, dated Mar. 18, 2014, 4 pages.

* cited by examiner

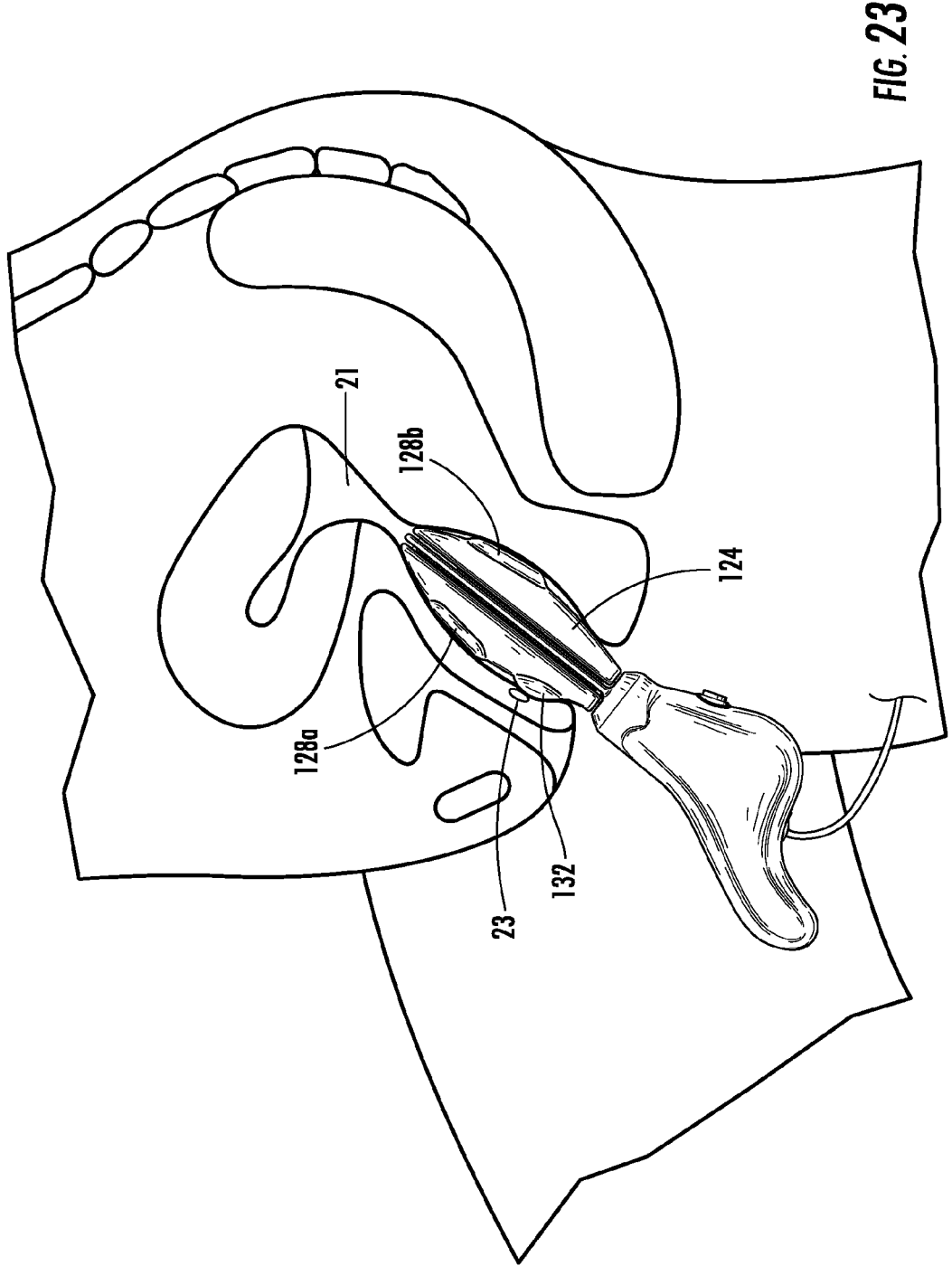

URINARY INCONTINENCE DEVICE AND METHOD AND STIMULATION DEVICE AND METHOD

CROSS-REFERENCE TO RELATED PATENT APPLICATIONS

This application is a Continuation of U.S. application Ser. No. 13/458,734, filed on Apr. 27, 2012, titled "Stimulation Device and Method", which is related to and claims priority to PCT Application No. PCT/US2011/040714, filed on Jun. 16, 2011, titled "Urinary Device and Method and Stimulation Device and Method", which is related to and claims priority to U.S. Provisional Application No. 61/430,072, filed Jan. 5, 2011, and to U.S. Provisional Application No. 61/355,822, filed Jun. 17, 2010, all of which are incorporated herein by reference in their entireties. This application is also a Continuation of U.S. application Ser. No. 13/739,750, filed Jan. 11, 2013, titled "Urinary Incontinence Device and Method", which is a Continuation of U.S. application Ser. No. 13/458,857, filed Apr. 27, 2012, titled "Urinary Incontinence Device and Method", which claims priority to PCT Application No. PCT/US2011/040714, filed Jun. 16, 2011, titled "Urinary Device and Method and Stimulation Device and Method", which is related to and claims priority to U.S. Provisional Application No. 61/430,072, filed Jan. 5, 2011, and to U.S. Provisional Application No. 61/355,822, filed Jun. 17, 2010, all of which are incorporated herein by reference in their entireties.

BACKGROUND

The present disclosure relates generally to the field of nerve and muscle stimulation. One aspect of the present disclosure relates to a device and method for electronic nerve and muscle stimulation, and in particular, internal tissue stimulation. The present disclosure relates specifically a device and method for various medical applications, including the treatment of urinary incontinence in females. Another aspect of the present disclosure also relates specifically to a device and method for creating a pleasurable sensation in a user using electronic nerve and muscle stimulation and/or vibrational nerve and muscle stimulation.

Urinary incontinence in females has numerous causes but is frequently tied to the weakening of pelvic floor muscles. Some studies have indicated a high success rate at relieving incontinence symptoms by strengthening pelvic floor muscles. Certain exercises may be performed to strengthen muscles in this area. However, the efficacy of daily exercises is dependent on patient compliance with the prescribed exercise regimen and patient compliance with the exercise regimen may be poor.

Some studies have indicated that more tightened and toned pelvic floor muscles increase the power and intensity of the female orgasm. Certain exercises may be performed to strengthen muscles in this area. Further, stimulation of particular nerves and muscles may be used to generate a pleasurable or enjoyable feeling.

SUMMARY

One embodiment of the disclosure relates to a method for treating urinary incontinence including providing a device having an expandable portion having an outer surface, a first electrode, and a second electrode, the first and second electrodes coupled to the outer surface of the expandable portion and configured to cause a contraction of a muscle in communication with the electrodes. The method further includes causing the expandable portion to inflate such that the first and second electrodes contact vaginal walls and causing a contraction of a muscle in communication with the electrode.

Another embodiment of the disclosure relates to an apparatus for the treatment of urinary incontinence including a shaft and a balloon surrounding at least a portion of the shaft. The device further includes an electrode coupled to a first portion of the balloon, the electrode configured to cause a contraction of at least one muscle in communication with the electrode, and a second portion of the balloon having a thickness less than the first portion of the balloon. The balloon inflates in a radially non-uniform manner in response to the difference in thicknesses of the first portion and the second portion.

Another embodiment of the disclosure relates to a system for treating urinary incontinence including a member comprising an expandable portion, an electrode disposed on the expandable portion, a memory, and processing electronics configured to cause a stimulation of a user's vaginal muscle in communication with the electrode in response to data stored in the memory.

Another embodiment of the disclosure relates to a stimulation device for creating a pleasurable sensation in a user including an expandable portion configured to assume a plurality of states of expansion between minimum expansion and maximum expansion and a vibrating element extending away from the outer surface of the expandable portion.

Another embodiment of the disclosure relates to a stimulation device for creating a pleasurable sensation in a user including a shaft having a proximal end and a distal end, the proximal end being interconnected to a housing, and an operative portion located between the proximal end and the distal end and configured to be located within a vagina when the device is in an inserted position. Only one balloon circumferentially surrounds the operative portion of the shaft, and a first electrode and a second electrode are coupled to the outer surface of the balloon and configured to cause a contraction of a muscle in communication with the electrodes. The balloon is configured to inflate such that the first and second electrodes press against at least one vaginal wall.

Another embodiment of the disclosure relates to a method of toning pelvic floor muscles including providing a device having an expandable portion having an outer surface, a first electrode, and a second electrode, causing the expandable portion to inflate such that electrodes contact at least one vaginal wall, and causing a contraction of a muscle in communication with the electrode. The first and second electrodes are coupled to the outer surface of the expandable portion and configured to cause a contraction of a muscle in communication with the electrodes.

Another embodiment of the disclosure relates to a stimulation device for creating a pleasurable sensation in a user including a shaft having a proximal end and a distal end, the proximal end being coupled to a handle, an operative portion located between the proximal end and the distal end and configured to be located within a vagina when the device is in an inserted position, and an expandable portion comprising an outer surface and configured to assume a plurality of states of expansion between minimum expansion and maximum expansion, the expandable portion circumferentially surrounding the operative portion of the shaft. The device further includes a first electrode, a second electrode, a first vibrating element, and a second vibrating element, the first electrode coupled to a first portion of the outer surface of the expandable portion, the second electrode coupled to a second portion of the outer surface of the expandable portion, the first and second electrodes configured to cause a contraction of a muscle in communication with the electrodes, the first vibrating element extending away from the outer surface of the expandable portion and configured to impart vibration to a user's Gräfenberg Spot; and the second vibrating element configured to impart vibration to a first portion of user's body. The device further includes a pump in communication with the expandable portion and configured to cause inflation of the expandable portion such that at least one of the first electrode, the second electrode, and the first vibrating element press against a vaginal wall, and processing electronics configured to cause an electrical signal in the electrodes, to control an aspect of vibration of the first vibrating element, and to control an aspect of vibration of the second vibrating element.

BRIEF DESCRIPTION OF THE DRAWINGS

FIG. 23 is a schematic sagittal cross-sectional view of a user with the device of FIG. 1 in an inserted position, shown according to an exemplary embodiment.

DETAILED DESCRIPTION

Figure 1:
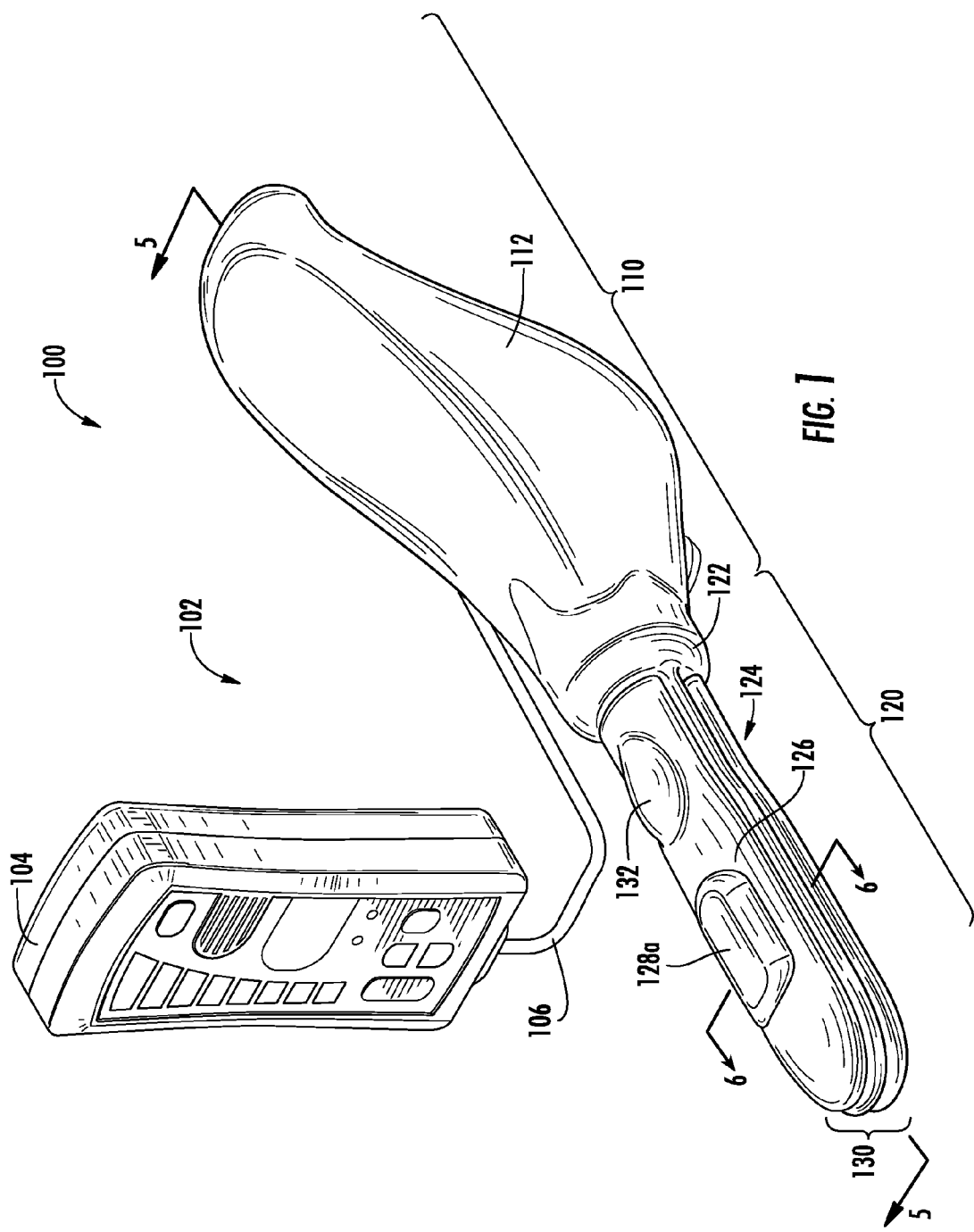
FIG. 1 is a perspective view of a medical device, shown according to an exemplary embodiment.

Referring generally to FIGS. 1-11 and 23, a medical device and method of treatment are shown according to exemplary embodiments. According to the embodiments shown, the medical device 100 generally includes a handle 110 and a probe 120, the probe 120 configured for insertion into a vagina. The probe 120 includes an inflatable member or balloon 124 on the outer surface of which at least one electrode 128 is disposed. An inflation device may be located in the handle 110 and configured to cause the balloon 124 to inflate, in turn causing at least one of the electrodes 128 to press against at least one vaginal wall. The balloon 125 may be inflated to a plurality of different inflated positions between fully deflated and fully inflated. A controller 104 interconnected with the handle 110 includes processing electronics 800 configured to control the electrodes 128 such that the electrodes 128 cause a contraction of a muscle in communication with an electrode 128.

According to an exemplary embodiment, the device and method for treating incontinence deliver electrical pulses to stimulate muscle contraction to strengthen the muscles in the area of the pelvic floor. Electrical stimulation causes muscles to contract and release repeatedly, thereby strengthening those muscles. Urinary incontinence in general, and urinary incontinence in females specifically, may be treated by strengthening the muscles that are responsible for bladder control (e.g., the pelvic floor muscles) using internal electrical stimulation. While the method and device are described for the treatment of urinary incontinence, it is contemplated that this device may also be used for other medical purposes, for example, bowel incontinence, in which case references to a vagina would correspondingly refer to an anus and/or rectum. Persons skilled in the art can also adapt the method and device for other internal applications through other natural orifices or through surgically created orifices.

Referring generally to FIGS. 12-23, a stimulation device for creating a pleasurable sensation in a user and a method of toning pelvic floor muscles are shown according to exemplary embodiments. According to the embodiment shown, the device 101 includes a handle 111 and a probe 121, the probe 121 configured for insertion into a vagina. The probe 121 includes an inflation member or balloon 125 having an outer surface 127. The balloon 125 may be configured to assume a plurality of states of expansion between minimum expansion and maximum expansion. According to one embodiment, a first electrode 129a, a second electrode 129b, and a first vibrating element [shown as a Gräfenberg Spot (G-Spot) stimulator 133] are disposed on the outer surface of the balloon 125. A second vibrating element (shown as a clitoral stimulator 141) is shown disposed on the handle 111. An inflation device may be located in the handle 111 and configured to cause the balloon 125 to inflate, in turn causing at least one of the electrodes 129 to press into contact with at least one vaginal wall. Processing electronics 801 may be located in the handle 111 and configured to control the current and voltage provided to the electrodes 129 such that the electrodes 129 cause a contraction of a muscle in communication with an electrode 129. The processing electronics 801 may also be configured to control at least one aspect of one or more vibrating elements 133, 141.

According to one embodiment, devices and methods described for toning pelvic floor muscles deliver electrical pulses to stimulate muscle contraction to strengthen the muscles in the area of the pelvic floor. Electrical stimulation causes muscles to contract and release repeatedly, thereby strengthening those muscles. Toning and tightening pelvic floor muscles improves intimate health and may increase the power and intensity of the female orgasm. Electrical tissue stimulation may also provide a pleasurable sensation to the user. While the method and device are described for vaginal stimulation and pelvic floor toning, it is contemplated that this device may cause pleasurable sensations to a user or tone pelvic floor muscles via the anus and rectum, in which case, references to vagina would be modified accordingly.

Before discussing further details of the devices, it should be noted that references to "front," "rear," "right," and "left" in this description are merely used to identify the various elements as they are oriented in the FIGURES, with "right," "left," "front," and "rear" being relative to a specific direction. These terms are not meant to limit the element which they describe, as the various elements may be oriented differently in various applications.

It should further be noted that for purposes of this disclosure, the term coupled means the joining of two members directly or indirectly to one another. Such joining may be stationary in nature or moveable in nature and/or such joining may allow for the flow of fluids, electricity, electrical signals, or other types of signals or communication between the two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

Referring to FIG. 1, a perspective view of a device 100 is shown according to an exemplary embodiment. As described below, device 100 may be used for the treatment of urinary incontinence, specifically in women. According to the exemplary embodiment shown, device 100 includes a probe assembly 102 which includes a housing, shown as handle 110, and a probe 120. Handle 110 provides the user a region which may be grasped for control and manipulation of the probe assembly 102. Handle 110 may facilitate insertion, positioning, and removal of probe 120. Handle 110 is shown to include a sleeve 112 configured to cover the majority of handle 110. Sleeve 112 is preferably pliable and provides a smooth and watertight surface to handle 110. The smooth and watertight surface facilitates cleaning which is beneficial due to the handle's 110 proximity to bodily fluids and the vaginal opening during use. Sleeve 112 may be translucent to allow lights (e.g., lamps, LEDs, displays, etc.) within handle 110 to shine through. Further, sleeve 112 may be customizable, e.g., bearing various colors or logos. Preferably, sleeve 112 is formed from silicone rubber.

According to the embodiment shown, probe 120 generally has the form of an elongated cylinder having an open proximal end and a closed distal end. Probe 120 may include a neck portion 122 near the proximal end. Probe 120 includes a member or expandable portion, shown as balloon 124. According to the exemplary embodiment, balloon 124 includes a single inflatable balloon having an outer surface 126. According to alternate embodiments, the expandable portion may include a plurality of balloons. According to various embodiments, the plurality of balloons may be oriented axially, radially, circumferentially, or some combination thereof. Balloon 124 may be formed of an airtight, elastic, biocompatible material, such as silicone rubber. According to alternate embodiments, balloon 124 may be formed of any suitable material.

Figure 2:
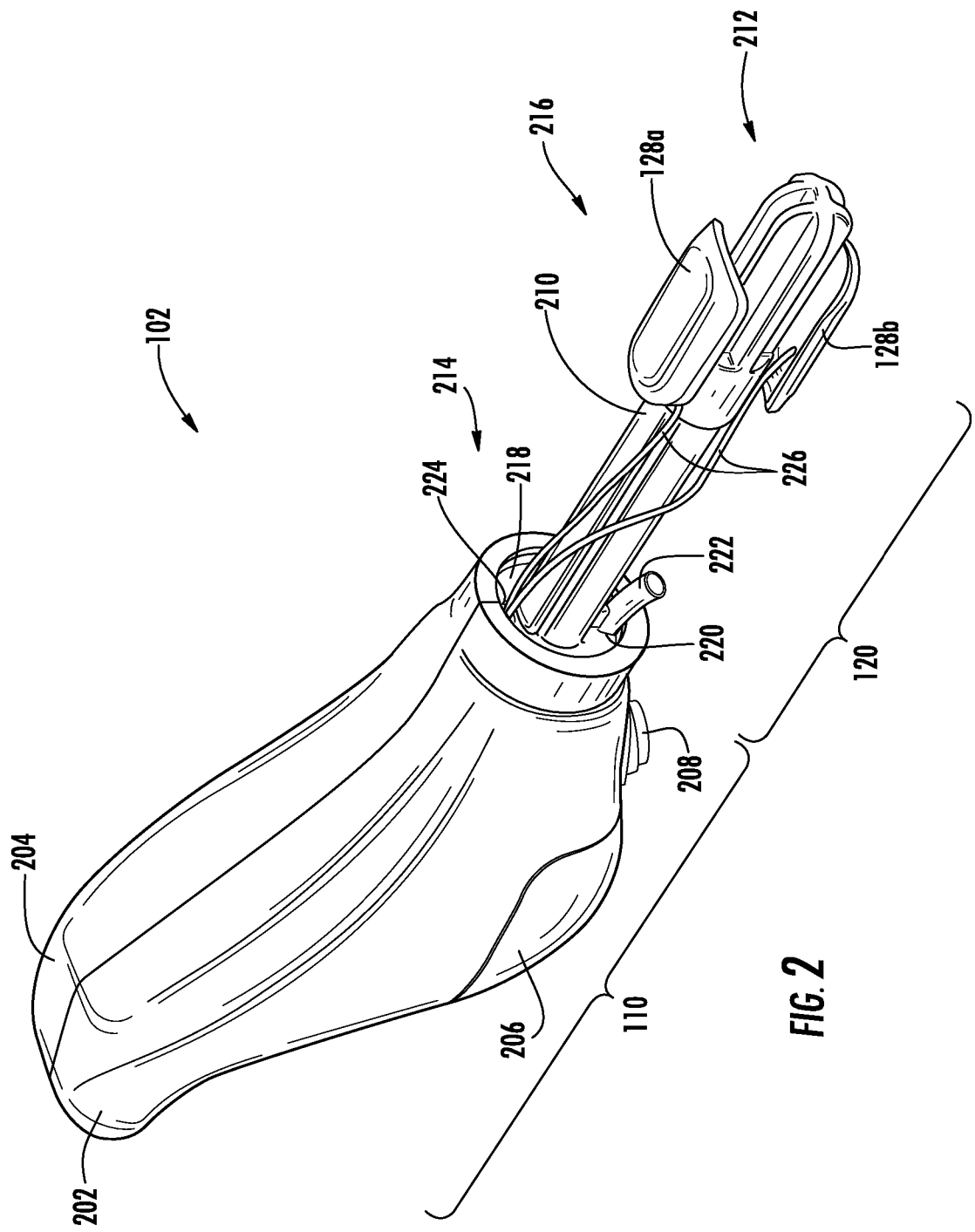
FIG. 2 is a perspective view of a portion of the device of FIG. 1, shown according to an exemplary embodiment.

Probe 120 is further shown to include at least one electrode 128, shown as electrode 128a (e.g., first electrode, top electrode, etc.). Preferably, electrode 128 is mounted to outer surface 126 of balloon 124 in such a manner that electrode 128 may come into contact with tissue adjacent to balloon 124 when probe 120 is in an inserted position. Referring briefly to FIG. 2, probe 120 may include a second electrode 128b (e.g., bottom electrode, etc.). First electrode 128a and second electrode 128b are shown radially opposite one another; however, probe 120 may have a plurality of electrodes 128, the plurality of electrodes being located anywhere on probe 120, e.g., left and right sides, both on top, axially or circumferentially offset, or equally or unequally spaced circumferentially around probe 120. The relative position of the electrodes 128 is dependent upon the particular tissue to receive the electrical stimulation. The placement and relative spacing of the electrodes will determine, in part, the effectiveness of the muscle contraction as a result of the electrical stimulation. According to various embodiments, a plurality of electrodes may be energized at the same time, different electrodes (e.g., a subset of a plurality of electrodes) may be actuated during different phases of a treatment session, or different electrodes may be actuated during different treatment sessions. For example, an even number of electrodes 128 may be actuated in pairs, or an odd number of electrodes may be actuated in a rotating pattern. Actuating different electrodes 128 at different times may cause different muscles to contract, thereby strengthening more and different pelvic floor muscles and preventing the muscles from becoming adjusted or de-sensitized to the electrical stimulation. The plurality of electrodes 128 may have the same or different shape. Electrode 128 is configured to deliver electrical pulses (e.g., signals, currents, voltages, frequencies, etc.) to stimulate muscle contraction to strengthen the muscles in the area of the pelvic floor. Electrode 128 may also communicate a response information (e.g., a signal indicative of the contractive force of the muscles) to processing electronics. According to one embodiment, the response information is a voltage created by the contracting muscle. According to another embodiment, the response information is an electric potential difference between first electrode 128a and second electrode 128b. The muscle contraction causing the response information may be caused by electrode stimulation of the muscle or may be the result of a manual contraction caused by the user.

According to the exemplary embodiment, electrodes 128 may be formed from stainless steel, and in another embodiment, the electrodes may be formed from an expandable, conductive silicone rubber or any other suitable material. It may be desirable to limit electrodes 128 from expanding so as to maintain a relatively consistent conductivity or to prevent the muscle stimulation from moving as balloon 124 is expanded. Further, electrodes formed of materials different than balloon 124 may not expand at the same rate as balloon 124 during inflation. Therefore, it may be beneficial to provide a balloon 124 which expands non-uniformly.

According to the exemplary embodiment, electrode 128a is supported by a first portion of balloon 124. The first portion of balloon 124 and a second portion of balloon 124 cooperate to cause balloon 124 to expand in a radially and/or circumferentially non-uniform manner relative to probe 120. Similarly, electrode 128b is supported by a third portion of balloon 124. The first and third portions of balloon 124 cooperate to cause balloon 124 to expand in a radially and/or circumferentially non-uniform manner relative to probe 120. Non-uniform expansion of balloon 124 may cause balloon 124 to substantially contour to the anatomy of a user, for example, to conform to the contours of the user's vagina. Non-uniform expansion of balloon 124 may also facilitate a suitable and comfortable fit of balloon 124 for the user.

Figure 5:
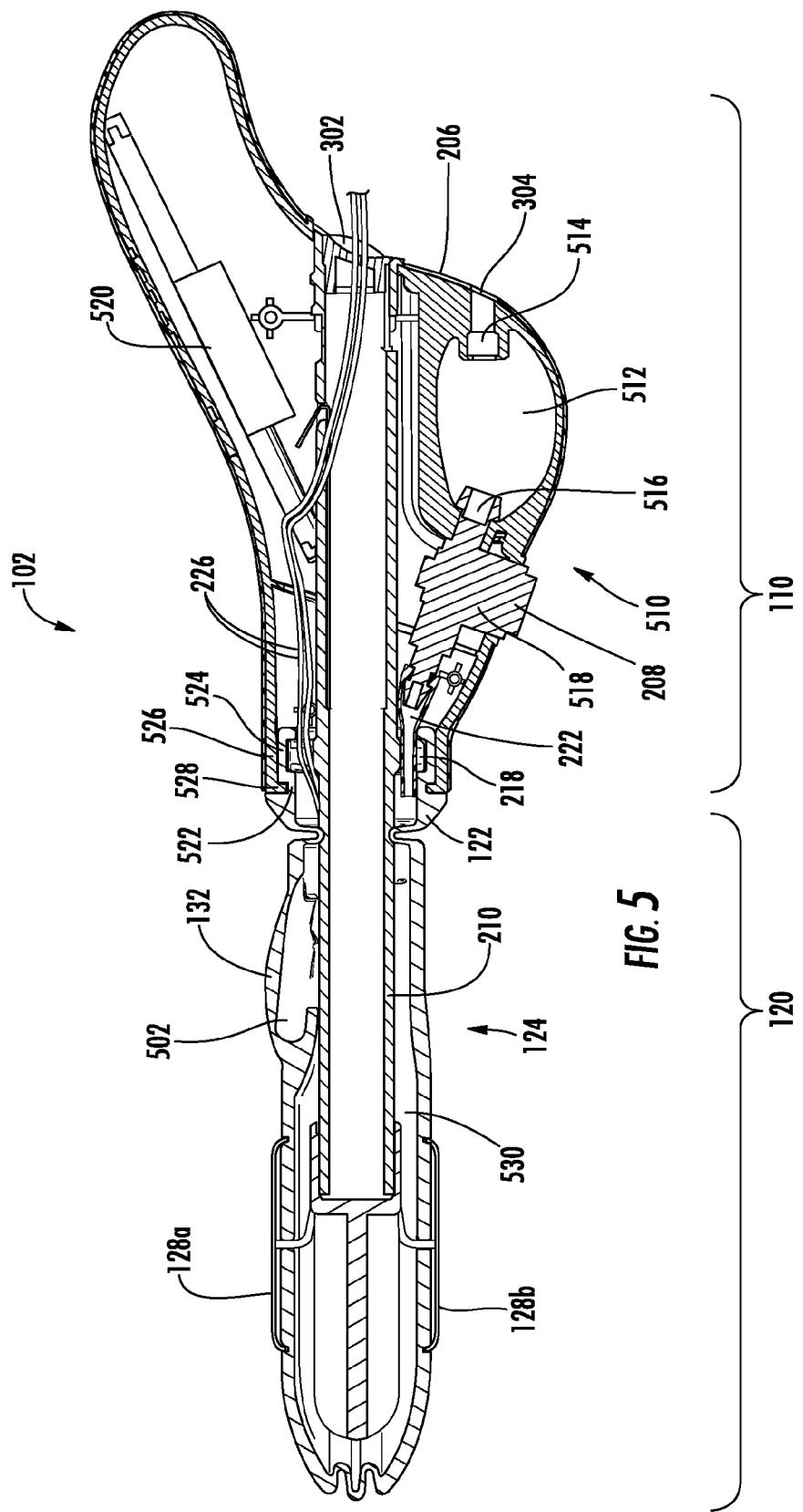
FIG. 5 is a longitudinal cross-section view of the device taken along line 5-5 of FIG. 1, shown according to an exemplary embodiment.
Figure 6A:
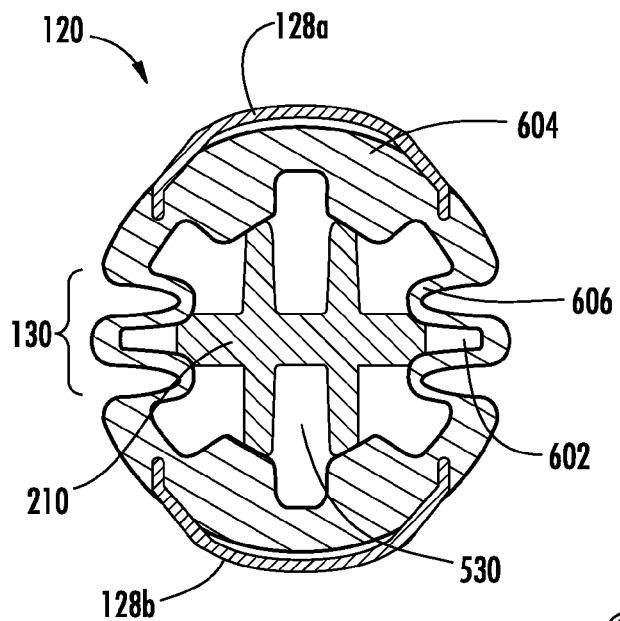
FIG. 6A is a radial cross-section view of the device taken along line 6-6 of FIG. 1 in a deflated state, shown according to an exemplary embodiment.

According to one embodiment, the second portion may be an expansion portion (e.g., folds, pleats, articulation, etc.), shown as bellows 130. The folds of bellows 130 provide a region of increased surface area of balloon 124 in the deflated state, which allows balloon 124 to expand in a circumferentially non-uniform manner. As shown, bellows 130 extend longitudinally or axially along the sides of balloon 124. Bellows 130 are further shown to extend around the distal end of balloon 124. Accordingly, bellows 130 are shown to extend substantially continuously around the midsection (e.g. equatorially region) of balloon 124. According to various alternate embodiments, bellows 130 may extend discontinuously, in a top/bottom meridian formation, or in any suitable orientation to cause differential expansion of balloon 124. Probe 120 may include any number of bellows 130 equally or unequally spaced around probe 120. Referring briefly to FIGS. 5 and 6A, bellows 130 may be configured to provide an opening 602 through which wires 226 may pass when balloon 124 is in a deflated state. According to the exemplary embodiment, bellows 130 are configured such that a majority of the expansion of balloon 124 occurs in the bellows region.

Figure 6B:
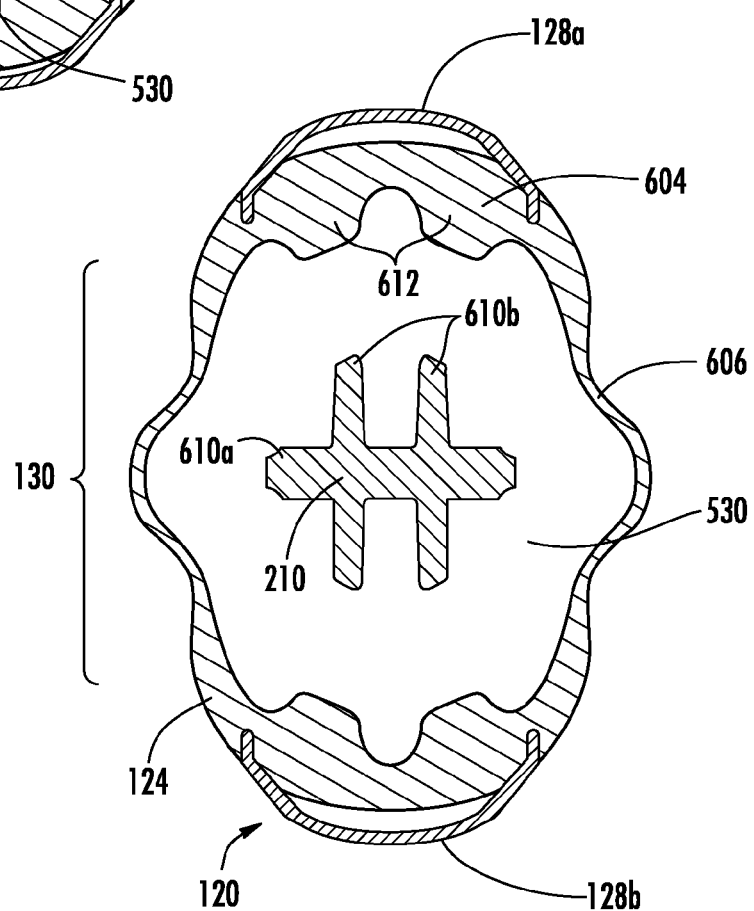
FIG. 6B is a radial cross-section view of the device taken along line 6-6 of FIG. 1 but showing the device in an inflated state, according to an exemplary embodiment.

Referring now to FIG. 6A, a radial cross-section of probe 120 is shown in a first state (e.g., minimum expansion, contracted, deflated, etc.), whereas FIG. 6B shows a radial cross-section of probe 120 in a second state (e.g., expanded state, inflated, etc.). As seen in the first, deflated state, bellows 130, first and third portions of balloon 124 are closely adjacent to or abut shaft 210. However, in the second, or expanded state, bellows 130 have substantially unfolded allowing radial expansion of the first and third portions of balloon 124 and electrodes 128a and 128b provided thereon.

According to another embodiment, the first portion of balloon 124 may have a first thickness 604, and the second portion of balloon 124 may have a second thickness 606, specifically thickness 604 of the first portion being greater than thickness 606 of the second portion. Accordingly, the first portion tends to resist circumferential expansion and maintain its form when balloon 124 is inflated. The second portion provides a "path of least resistance" for expansion, such that for a prescribed level of inflation pressure, balloon 124 will stretch or expand the material of balloon 124 more in the second region than in the first region.

According to one embodiment, at minimum expansion, balloon 124 has a diameter of between approximately 1 inch and approximately 2 inches. Preferably, at minimum expansion, balloon 124 has a diameter of approximately 1⅛ inches. According to one embodiment, at maximum expansion, balloon 124 has a diameter of between approximately 2 inches and approximately 4 inches, the preferred maximum expansion of balloon 124 being between approximately 3 inches and approximately 4 inches in diameter. Expansion of balloon 124 in these ranges enables contouring balloon 124 to women of different anatomical sizes.

Returning to FIG. 1, probe assembly 102 may include a protrusion, shown as bump 132, located on a portion of probe 120. As shown, bump 132 is located on a top portion of the outer surface of balloon 124. Bump 132 may be used to indicate to a user that probe 120 is properly inserted. For example, bump 132 may provide a user a point of reference for internal positioning probe 120. According to the exemplary embodiment, bump 132 may include a cavity 502 (shown in FIG. 5), which may be configured to receive a sensor (e.g., capacitive sensor, pressure sensor, conductivity sensor, etc.), which will be discussed further below.

According to the exemplary embodiment, an electronic control unit, shown as controller 104, is connected to handle 110 via cable 106. In the embodiment shown, controller 104 is a handheld control unit (i.e., one that is sized to fit in the user's hand). Controller 104 includes a power supply 808, processing electronics 800, indicators (e.g., audio, visual, and/or haptic indicators), and input controls 704 which will be discussed in detail below. According to alternate embodiments, communication between controller 104 and probe assembly 102 may be wireless, for example, using Bluetooth, wireless local area network, or personal area network protocols. According to various other embodiments, any or all of the components of controller 104 may be located on or in probe assembly 102.

Referring to FIG. 2, a perspective view of a portion of probe assembly 102 is shown with sleeve 112 and balloon 124 removed, according to an exemplary embodiment. Handle 110 may be formed of a plurality of portions, such as a "clam shell" assembly. As shown, handle 110 includes a left portion 202, a right portion 204, and a bottom portion 206, wherein left portion 202 and right portion 204 are hollow, substantially symmetric pieces of ABS plastic coupled together to form a housing. Bottom portion 206 may include an inflation device, wherein bottom portion 206 is formed of a deformable material, for example, a silicone rubber which sufficiently pliable to compress the inflation device and to return to shape. According to various alternate embodiments, bottom portion 206 may be a rigid portion movably coupled to left portion 202 and/or right portion 204. Left portion 202, right portion 204, and bottom portion 206 may be formed of any suitable material, may be formed of the same or different materials, or may be formed as one element. Portions of handle 110 may be coupled by snap fit, fastener, hinge, and/or any other suitable coupling technique. Handle 110 is further shown to include a release valve 208, discussed in detail below.

According the exemplary embodiment seen in FIGS. 2 and 4-6B, probe assembly 102 includes a shaft 210. As shown, shaft 210 is an elongated structure having a distal end 212 and a proximal end 214. According to the embodiment shown, proximal end 214 is coupled to handle 110 and interconnected to controller 104 via cable 106. Shaft 210 may include an operative region 216 located between proximal end 214 and distal end 212, the operative region 216 being configured to be substantially located within the vagina when probe 120 is in an inserted position.

As shown, shaft 210 includes a radially extending flange (e.g., collar), shown as bulkhead 218. Bulkhead 218 is configured to provide a substantially airtight seal between handle 110 and balloon 124. According to the exemplary embodiment, bulkhead 218 includes a first passage, shown as bottom passage 220, and a second passage, shown as top passage 224. Bottom passage 220 may be configured to allow a conduit, shown as tube 222, to extend from an inflation device into balloon 124. A substantially airtight seal is preferably formed (e.g., with silicone glue) between tube 222 and bulkhead 218. Top passage 224 may be configured to allow wires 226 to pass from electrodes 128 and/or other sensors or motors into handle 110. A substantially airtight seal may be formed (e.g., with silicone glue) between wires 226 and bulkhead 218. Bulkhead 218 may have any number of passages, and the passages may have any orientation around shaft 210. Alternatively, bulkhead 218 may include one passage for passing both tube 222 and wires 226.

Shaft 210 may be solid, hollow, or any combination thereof. According to one embodiment, shaft 210 may be configured to house batteries used to power device 100 or components thereof. According to another embodiment, tube 222 and/or wires 226 may be routed through shaft 210. According to yet another embodiment, shaft 210 may include perforations configured to allow pressurizing fluid pumped through shaft 210 to enter into balloon 124. Routing pressurizing fluid, tube 222, and/or wires 226 through shaft 210 may eliminate the need for passages 220, 224 through bulkhead 218. Accordingly, these passages may be removed in order to improve the airtight seal between handle 110 and balloon 124.

Figure 3:
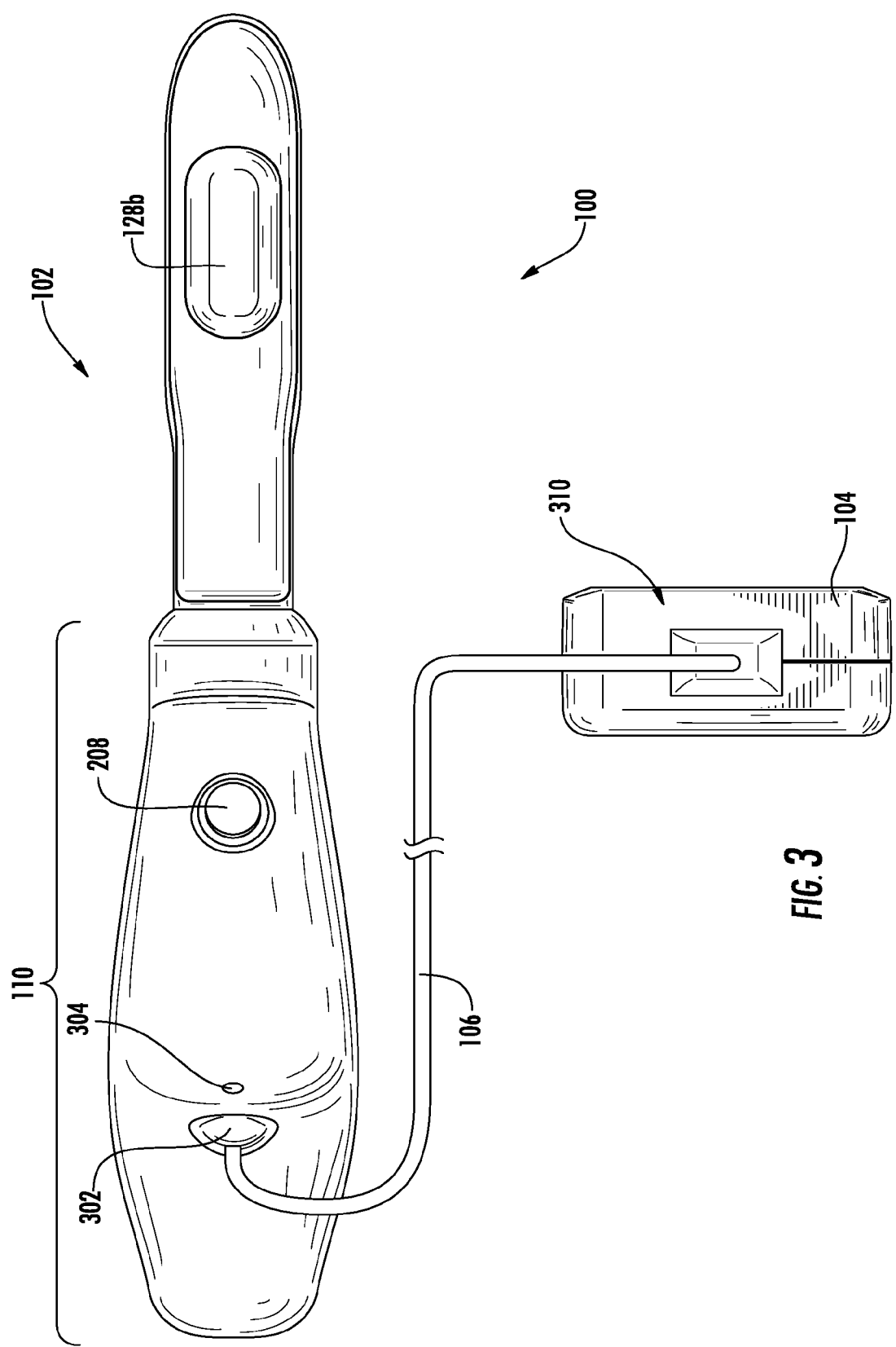
FIG. 3 is a bottom plan view of the device of FIG. 1, shown according to an exemplary embodiment.

Referring to FIG. 3, a bottom view of device 100 is shown according to an exemplary embodiment. Handle 110 includes a coupling point 302 configured to receive cable 106. Coupling point 302 may be a jack or orifice in handle 110. According to the exemplary embodiment, coupling point 302 is a cap forming an end portion of shaft 210 and configured to allow wires 226 to pass out of handle 110. Handle 110 is further shown to include structure such as air inlet 304 (or orifice, valve, grommet, etc.) for inflation of balloon 124 described further below.

The diameter of balloon 124 may be substantially uniform over the length of probe 120, or the diameter of balloon 124 may vary. As shown, proximal end 214 of balloon 124 has a first diameter, and distal end of balloon 124 has a second diameter, the second diameter being greater than the first diameter. According to one embodiment, probe 120 transitions from the first diameter to the second diameter between neck portion 122 and electrode 128. According to the embodiment shown in FIGS. 3 and 5, balloon 124 begins to transition from the first diameter to the second diameter proximate bump 132. Varying the diameter of balloon 124 along the length of probe 120 effects the expansion of balloon 124 along the length of probe 120. For example, the smaller proximal diameter limits expansion at proximal end 214 while allowing greater expansion near of balloon 124 near electrodes 128 and proximal end 212, thereby contouring balloon 124 to the vaginal cavity. This further enables electrodes 128 to press against vaginal walls without applying excessive pressure on the introitus (vaginal entrance).

Figure 4:
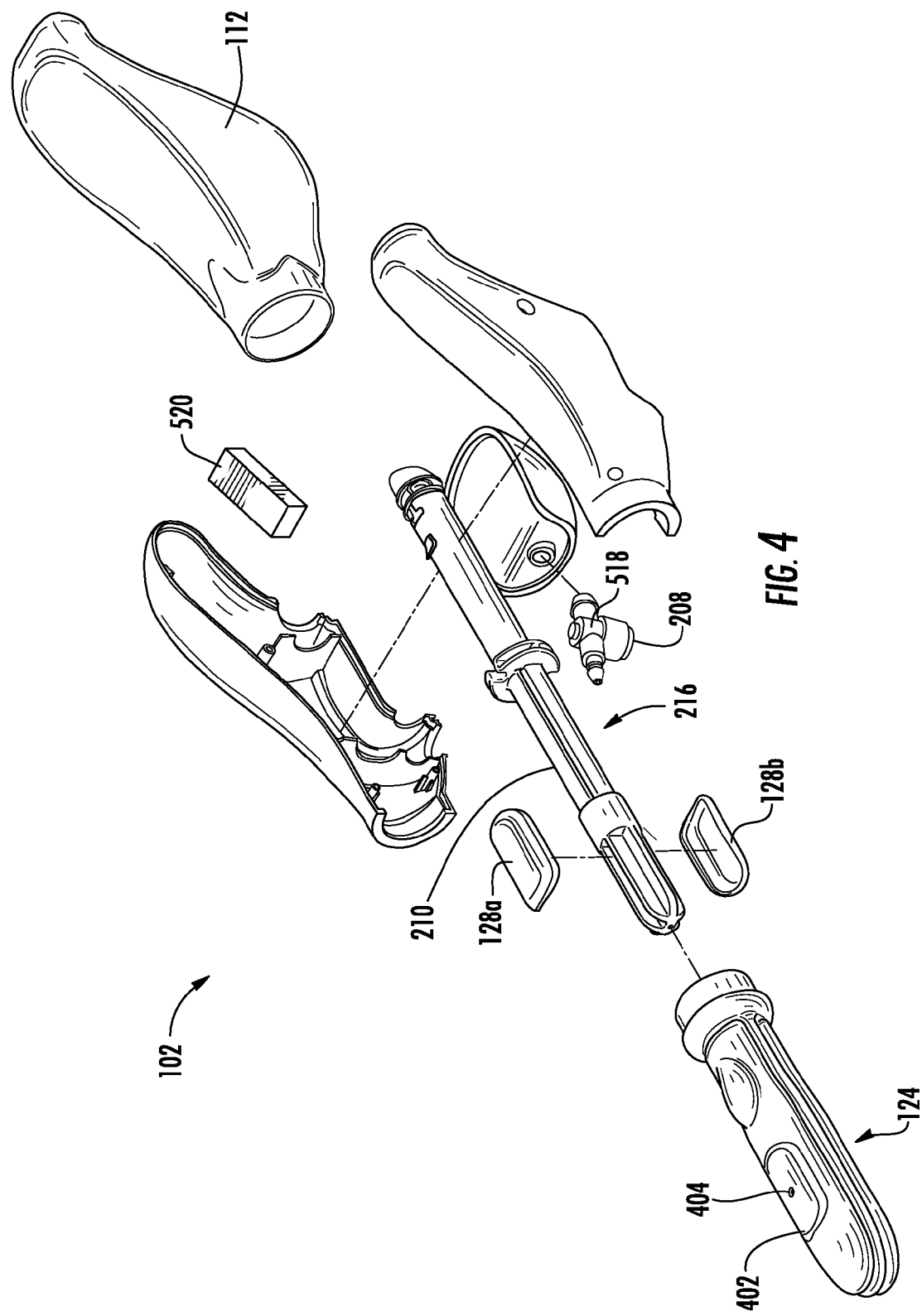
FIG. 4 is an exploded perspective view of a portion of the device of FIG. 1, shown according to an exemplary embodiment.

Referring to FIG. 4, a partially exploded view of probe assembly 102 is shown with tube 222 and wires 226 removed for clarity, according to an exemplary embodiment. As shown, balloon 124 includes a depression, cavity, or pocket 402 configured to receive electrode 128. According to an exemplary embodiment, a periphery of electrode 128 is configured to seat into pocket 402, and a sealant (e.g., silicone glue) may be used to couple electrode 128 to pocket 402 and to form a substantially airtight seal between electrode 128 and balloon 124. Forming a seal between an outer periphery of electrode 128 and balloon 124 achieves the added benefit of preventing fluid or debris from getting underneath electrode 128, thereby facilitating sanitary maintenance of probe 120. Balloon 124 is further shown to include an aperture, shown as hole 404, which is configured to permit passage of wires 226 from electrode 128 to the interior of balloon 124. A sealant may be used to retain wires 226 in place and to form a substantially airtight seal between wires 226 and balloon 124.

According to the embodiment shown, probe 120 comprises only one balloon 124 configured to surround operative region 216 of shaft 210. Referring briefly to FIG. 23, singular balloon 124 is shown to surround the entire portion of shaft 210 located within a vagina 21 when probe 120 is in an inserted position. According to various embodiments, probe 120 is in an inserted position when electrodes 128 are located within the vagina 21 or when bump 132 is proximate a user's Gräfenberg Spot (G-Spot) 23. Use of a single balloon has the benefit of minimizing costs (assembly and material) while also simplifying the structure of the device.

Referring to FIG. 5, a longitudinal cross-section of probe assembly 102 is shown according to an exemplary embodiment. Balloon 124 is shown to define a lumen or cavity 530, and cavity 530 is configured to receive shaft 210. Balloon 124 is shown to circumferentially surround at least a portion of shaft 210.

Probe assembly 102 is shown to include an inflation device located at least partially within bottom portion 206 of handle 110 for selectively inflating and deflating balloon 124. According to an exemplary embodiment, the inflation device includes a pump 510 which may be manually operated. Pump 510 includes a cavity within bottom portion 206, shown as bladder 512, and a first check valve 514 is located between bladder 512 and air inlet 304. Check valve 514 permits air to enter bladder 512 through air inlet 304 from outside of probe assembly 102 and prevents air from exiting back through air inlet 304 when bladder 512 is compressed. A second check valve 516 is located between tee connector 518 and bladder 512. Check valve 516 permits air to enter tee connector 518 from bladder 512 and prevents air from back flowing into bladder 512, for example, when bladder 512 expands.

As shown, tee connector 518 couples bladder 512, release valve 208, and tube 222. Release valve 208 may be of any suitable mechanism to permit air under pressure to be selectively released from balloon 124, for example a thumbscrew or a pushbutton. Release valve 208 may also act as a relief valve to prevent over-pressurization of balloon 124. Tube 222 extends from an outlet of tee connector 518 through bulkhead 218 into probe 120. In operation, squeezing bottom portion 206 compresses bladder 512 and forces air through tee connector 518 and tube 222 into balloon 124. When the squeezing force exerted on bladder 512 is released, bladder 512 will resume its natural, inflated position as air is drawn into bladder 512 through check valve 514. Bladder 512 is squeezed and released repeatedly to force pressurized air into balloon 124. Increased pressure in balloon 124 eventually causes inflation of balloon 124, which in turn causes electrode 128 to contact a vaginal wall. According to one embodiment, the level of inflation of balloon 124 is controlled by a user and may be selected to ensure a suitable and comfortable fit between balloon 124 and the user's vagina. According to another embodiment, the appropriate level of inflation is communicated to the user by a health care professional. According to another embodiment, the appropriate level of inflation is stored in memory 920 of processing electronics 800 described below. According to various alternate embodiments, the inflation device may include a motorized pump, the inflation device may be located in controller 104 and pressurized air directed into balloon 124 through flexible tubing, and/or the inflation device may be located within probe 120. As described, the pressurizing fluid of the exemplary embodiment is air; however, any suitable pressurizing fluid may be used, for example, water, saline, oil, or other gases or liquids.

According to an exemplary embodiment, device 100 may include a pressure sensor 520, located in handle 110 and barometrically connected to balloon 124. According to one embodiment, a sampling tube extends from the interior of balloon 124 to pressure sensor 520. According to other embodiments, a sampling tube may extend from tube 222 or tee connector 518 to pressure sensor 520. According to other embodiments, pressure sensor 520 may be located in-line with tube 222, located in probe 120, for example in cavity 502, or located in controller 104. Pressure sensor 520 may visually display an indication of pressure on handle 110, for example, a gauge, a light, a digital display, etc. According to an exemplary embodiment, pressure sensor 520 is configured to communicate (via wires or wirelessly) pressure information to processing electronics 800. For example, pressure sensor 520 may generate a response information, e.g., a signal indicative of the contractive force of the muscles on balloon 124. The response information may correlate to a rise in pressure created in balloon 124 by the contracting muscle acting on balloon 124. The response information may be triggered by the electrical stimulation provided by electrodes 128 or may be triggered by the user manually (e.g., consciously, volitionally, voluntarily, etc.) forcing a contraction of her pelvic floor muscles.

According to an exemplary embodiment, neck portion 122 of probe 120 includes an external annular groove 522 and an internal annular groove 524. Internal annular groove 524 is configured to fit over a radial periphery of bulkhead 218, and a sealant (e.g., silicone glue) may be used between internal annular groove 524 and bulkhead 218 to form a substantially airtight seal. Proximate bulkhead 218, left handle portion 202 and right handle portion 204 cooperate to form a substantially cylindrical portion 526 and an inwardly extending annular flange 528. Substantially cylindrical portion 526 fits over neck portion 122 of probe 120 and helps to hold internal annular groove 524 against bulkhead 218. Inwardly extending flange 528 fits into external annular groove 522 of probe 120. Accordingly, neck portion 122 and handle 110 are configured to prevent balloon 124 from slipping free of handle 110.

Referring to FIGS. 6A and 6B, shaft 210 is shown to be axially located within cavity 530 of probe 120. According to the exemplary embodiment, shaft 210 is configured to provide sufficient rigidity to probe 120 to facilitate insertion of probe 120 into a vagina. Shaft 210 may include a plurality of portions (e.g., members, structures, regions, webs, etc.), shown as ribs 610, configured to support balloon 124. Ribs 611a may support bellows 130 and inhibit bellows 130 from collapsing into cavity 530. Balloon 124 may include a plurality of structures (stiffeners, portions, etc.), shown as lugs 612, which are configured to rest on ribs 610b when balloon 124 is in a fully deflated state. Lugs 612 provide cushioning between shaft 210 and a user. Lugs 612 may also stiffen portions of balloon 124 underneath electrodes 128, thereby reducing flexure of balloon 124 in the area of the electrode. As shown, bellows 130, lugs 612 and ribs 610 are configured to cooperate to maintain a substantially round shape to probe 120 when balloon 124 is in a deflated state.

Figure 7:
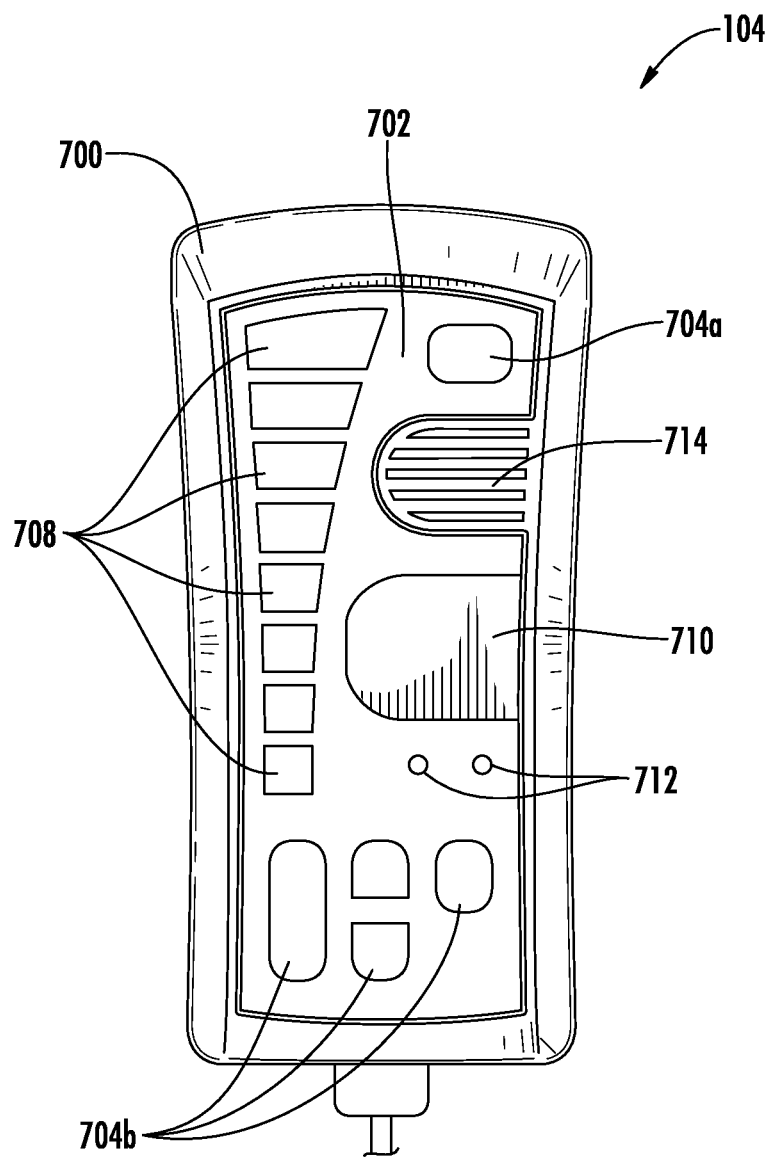
FIG. 7 is a front view of a control unit of the device of FIG. 1, shown according to an exemplary embodiment.

Referring to FIG. 7, a front view of controller 104 is shown according to an exemplary embodiment. As shown, controller 104 may include a housing 700, a front panel 702, and a cavity that receives one or more batteries to supply power to device 100. Front panel 702 may include a plurality of control inputs (e.g. toggles, switches, an electro-acoustic transducer configured to receive voice commands, a touch sensitive display, etc.), shown as buttons 704, configured to enable user input into controller 104. For example, button 704a may be a power button configured to turn controller 104 on and off. Button 704a may be a combination power/mode button configured to turn controller 104 on and off and to switch between operating states. According to an exemplary embodiment, buttons 704b may provide other control inputs, for example, stimulation select, pressure select, increase, decrease, pause, etc.

According to the embodiment shown, front panel 702 includes a plurality of sequentially oriented lamps 708 (e.g., lights, LEDs, etc.) configured to indicate the level of stimulation intensity and/or pressure inside balloon 124. Controller 104 may also include a display 710 configured to numerically indicate balloon pressure and/or stimulation intensity. Display 710 may be further configured to display videos, for example instructional videos, or to display a waveform representative of the stimulation signal. Display 710 and the plurality of lamps 708 may indicate the same or different information. Front panel 702 may include a plurality of indicator lamps 712 (e.g. lights, LEDs, etc.) which may indicate a power state (e.g., power on, battery low, etc.), a communication state (e.g., communication to a computer, to probe assembly 102, etc.), pressure state (e.g., the pressure inside balloon 124 has reached a predetermined value), an error state, etc. According to an alternate embodiment, controller 104 may include a touchscreen configured to both provide information to a user and to receive input from a user. Using a touchscreen would provide an easy to clean surface, thereby facilitating sanitary hygiene.

Controller 104 may also include an audio device, shown as speaker 714. Speaker 714 may be configured to provide motivation and/or audio instruction to a user. According to one embodiment, speaker 714 may announce that the pressure inside balloon 124 has reached a prescribed level. According to another embodiment, speaker 714 may request a user to force a contraction of the muscle in communication with electrodes 128.

Referring again to FIG. 3, cable 106 is shown to couple to controller 104 using connector 310. According to an exemplary embodiment, connector 310 is a D-sub-9 connector. According to alternate embodiments, any suitable connector may be used (e.g., a Universal Serial Bus connector). Cable 106 may be decoupled from controller 104, and controller 104 may then be coupled to a computer to receive firmware (e.g., configuration data) or protocol data updates from the computer. According to various alternate embodiments, controller 104 may wirelessly connect to a computer, controller 104 may include an interface which enables the protocol to be entered directly into controller 104, or cable 106 is configured to remain coupled to controller 104 and to de-couple from probe assembly 102.

Operation of device 100 is described below according to an exemplary embodiment. A method for treating urinary incontinence in a female includes inserting probe 120 into the vagina, pressurizing balloon 124 to inflate balloon 124 such that electrodes 128 contact the walls of the vagina (e.g., to place electrodes 128 snugly against the walls of the vagina to provide an electrical conduction pathway from the electrodes to the muscles and/or associated nerves), and periodically supplying a pulsed electrical stimulation to electrodes 128 to stimulate the muscles. In this manner, balloon 124 allows device 100 to ensure a proper fit with differing anatomies. As the muscles contract in response to the electrical stimulation, the muscle walls of the vagina exert a force on inflated balloon 124, and as the muscles contract, balloon 124 is compressed. Pressure sensor 520 generates a signal indicative of the contractive force of the muscles on balloon 124 triggered by the electrical stimulation provided through the electrodes 128. The signal from pressure sensor 520 may be communicated (e.g., via wired or wireless connections) to processing electronics 800. Processing electronics 800 may be configured to process the signal from pressure sensor 520 to determine information related to muscle contraction caused by the electrical stimulation (e.g., the force or strength of muscle contraction, the duration of muscle contraction, etc.). When muscle contraction stops, the air pressure within balloon 124 causes balloon 124 to expand to original inflated size. The method also includes using a biphasic pulse. The progress of the treatment can be monitored by evaluating the increase in strength of muscle activity by measuring muscle contraction over a number of treatment sessions. Urinary incontinence in general, and urinary incontinence in females specifically, may be treated by strengthening the muscles that are responsible for bladder control (e.g., the pelvic floor muscles) using internal electrical stimulation. This treatment may be useful for women who have become incontinent with age or women who have become incontinent due to recent childbirth. According to one embodiment, device 100 may be used three weeks after childbirth.

According to the exemplary embodiment described, processing electronics 800 supply a biphasic pulse of electrical current to electrodes 128 which in turn stimulates contraction of the muscles. For example, the biphasic pulse may have a first stimulation phase providing a pulse at 12 hertz for 6 seconds followed by a first rest period having a duration of 6 seconds. A second stimulation phase providing a pulse at 25 hertz for six seconds follows the first rest period, and a second rest period having a duration of 6 seconds follows the second phase. The use of a biphasic pulse (e.g., a pulse having two stimulation periods having different frequencies) prevents the muscles from becoming adjusted or de-sensitized to the electrical stimulation. This sequence of stimulation phases and rest phases repeats for a treatment period as necessary. A typical treatment period is approximately 15 minutes. In another embodiment, a multiphasic pulse (e.g., a plurality of different pulse durations and/or frequency between pulses) may be used. Within each stimulation phase, a symmetric alternating current may be applied to the muscle via electrodes 128 to reduce the effects of electrophoresis or cataphoresis on the muscle tissues. For example, applying a current of a positive first value for a first pulsewidth (e.g., 200 microseconds), applying no current for 40 microseconds, and then applying a current of a negative first value for a first value (e.g., 200 microseconds) limits the migration of ions with the muscle tissue. This pattern of alternating current pulsewidths may then be repeated at various frequencies (hertz), e.g., 12 hertz, 25 hertz, 50 hertz, etc. Accordingly, the amount of time between the end of the negative current until the beginning of the positive current depends on the frequency. Placing a short rest period (e.g., 40 microseconds) between the bipolar phases may improve circuit reliability.

In other embodiments, other frequencies and/or durations for the stimulation phases and/or rest periods may be used. For example, in one embodiment, the frequency delivered may be variable, and frequencies up to 50 hertz may be delivered. The current delivered during the stimulation phase may be substantially between 10 milliamps and 50 milliamps. According to another embodiment, electronics 800 supply a biphasic pulse of electrical potential between electrodes 128. The electrical potential between electrodes 128 may be substantially between 10 Volts and 50 Volts. It is believed that these ranges of current and voltage provide therapeutic benefit. According to another embodiment, stimulation may occur as low as 4-5 Volts. Contraction of the muscle is a function of current (or voltage) amplitude, pulsewidth, and frequency applied to the muscle. Further, the rate at which the muscle relaxes has a minimum persistence time that is affected by the strength and duration of the contraction. If the period (i.e., 1/frequency) of stimulation is greater than the minimum persistence time of the contraction, a user may perceive the stimulation as convulsions rather than a continuous contraction. Accordingly, processing electronics 800 may be configured to control one of frequency, pulsewidth, and amplitude in order to maintain a contraction perceived by the user as substantially continuous. According to one embodiment, processing electronics 800 may be configured to control one of frequency, pulsewidth, and amplitude based on the other two in order to maintain a substantially continuous contraction. Additionally, processing electronics 800 may be configured to ramp at least one of frequency, amplitude, and pulsewidth at the beginning and/or end of each phase. Ramping the frequency, amplitude, and/or pulsewidth may reduce the step function of stimulation entering a phase, which may be uncomfortable or startling for some users. According to one embodiment, the pulsewidth may be stepped up by a fraction of the desired pulsewidth (e.g., 50 microseconds) per cycle until the desired pulsewidth (e.g., 200 microseconds) is reached. Processing electronics 800 may inhibit certain combinations of frequency, current, and voltage. According to the exemplary embodiment described, a health care professional may cause the stimulation parameters to be stored in processing electronics 800. In various alternate embodiments, the user, via a control 704 located on the controller 104, may control the frequency of the electrical signal being supplied, may control the current delivered during each stimulation phase, or may control the voltage delivered during each stimulation phase.

According to an exemplary embodiment, protocol data 926 (e.g., prescribed pressure, prescribed stimulation frequency, amplitude, pattern, etc.) may be stored into memory 920 in controller 104 by a non-user of probe 120 (e.g., a healthcare professional). Controller 104 and probe assembly 102 may then be provided to the probe user (e.g., a patient); however, the probe assembly user cannot change the protocol. According to alternate embodiments, the probe user may change the protocol, or the probe user may download a healthcare professional prescribed protocol into memory 920 of controller 104.

Figure 8:
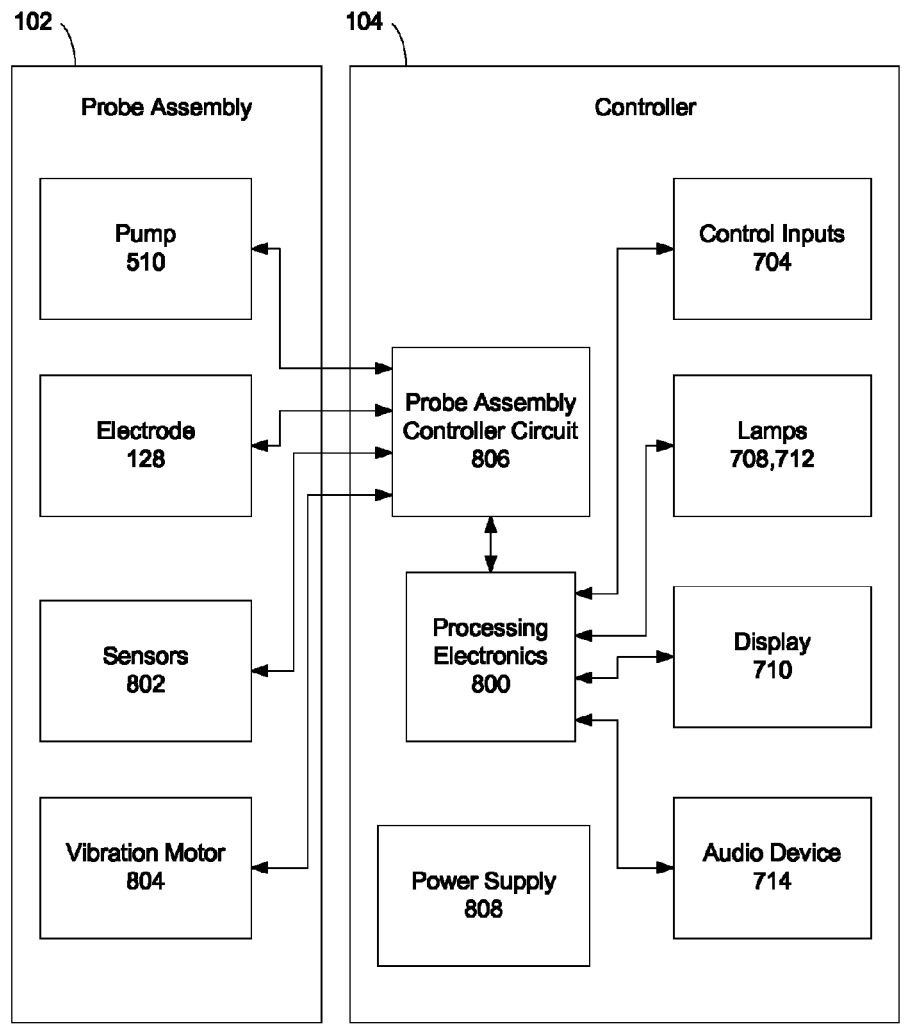
FIG. 8 is a schematic block diagram of the device of FIG. 1, shown according to an exemplary embodiment.

Referring to FIG. 8, a block diagram of device 100 is shown according to an exemplary embodiment. Probe assembly 102 is shown to include a pump 510, electrode 128, sensors 802, and vibration motor 804. Pump 510 is configured to cause inflation of balloon 124 and may be manually operated or motorized. First electrode 128a and/or second electrode 128b are configured to provide an electrical signal (e.g., current, voltage, frequency, etc.) to a muscle in communication with the electrode. According to various embodiments, probe assembly 102 may have one or a plurality of electrodes. Probe assembly 102 may include one or more sensors 802 (e.g., a capacitive sensor, a pressure sensor 520, a conductivity sensor, etc.). Sensors 802 may be disposed in any suitable location in probe assembly 102 (e.g., in handle 110, in cavity 502 under bump 132, etc.). Vibration motors 804 may be configured to provide haptic feedback to a user in response to user input through controls 704 or as an indication that balloon 124 has been inflated to a predetermined pressure. Alternatively, vibration motor 804 for may be located in cavity 502 under bump 132 and configured to provide a pleasurable sensation to a user. The pleasurable sensation may induce a user to maintain compliance with a prescribed treatment regimen. The pleasurable sensation may be used to cause an orgasm, which in turn causes a release of serotonin and norepinephrine in the user which may improve the user's mood and treat depression, specifically post-partum depression. In order to induce an orgasm, a clitoral stimulator (e.g., clitoral stimulator 141 shown in FIG. 12) may be added to probe assembly 102.

According to an exemplary embodiment, controller 104 includes control inputs 704, lamps 708, 712, display 710, audio device 714, processing electronics 800, probe assembly controller circuit 806, and power supply 808. The control inputs may include any suitable user interface, e.g., buttons 704, toggles, switches, an electro-acoustic transducer configured to receive voice commands, a touch sensitive display, etc. Lamps such as lamps 708, 712 may provide information to a user through illumination, brightness, color, blinking pattern, and/or illumination of a subset of a plurality of spatially oriented lamps. Display 710 may also be configured to provide alphanumeric or graphical images. Audio device 714 may be a speaker configured to provide aural information to a user and may be combined with or separate from the electro-acoustic transducer control input. Probe assembly controller circuit 806 is shown coupled to probe assembly 102 and may include any number of mechanical or electrical circuitry components or modules for a pump 510, electrode 128, sensors 802, and/or vibration motors 804 of probe assembly 102. For example, circuit 806 may be configured to send electrical signals to pelvic floor muscles while sending response information to processing electronics 800.

Controller 104 is further shown to include a power supply 808. Power supply 808 is configured to provide electrical power to device 100 and components thereof. According to an exemplary embodiment, device 100 is configured to be powered by a 6 Volt battery. According to other embodiments, device 100 may use other voltages, a rechargeable battery, or may be plugged into utility power supply. Power supply 808 or processing electronics 800 may be configured to increase the voltage and/or amperage available to electrodes 128, for example, up to 110V. According to one embodiment, the maximum electrical potential generated between the first electrode 128a and second electrode 128b is approximately 80 Volts. According to another embodiment, it is believed that the maximum therapeutic range of the electrical potential generated between first electrode 128a and second electrode 128b is approximately 50 Volts.

While the exemplary embodiment shows a separate probe assembly 102 and controller 104, it is contemplated that any or all of the components shown as part of controller 104 may be located in probe assembly 102. For example, lamps 708 and/or lamps 712 may be located on handle 110. Alternatively, control inputs 704, lamps 708, 712, display 710, audio device 714, processing electronics 800, and probe assembly controller circuit 806 may be located in handle 110, and power supply 808 (e.g., batteries) may be located in shaft 210. According to another embodiment, pump 510 may be located in controller 104.

Figure 9:
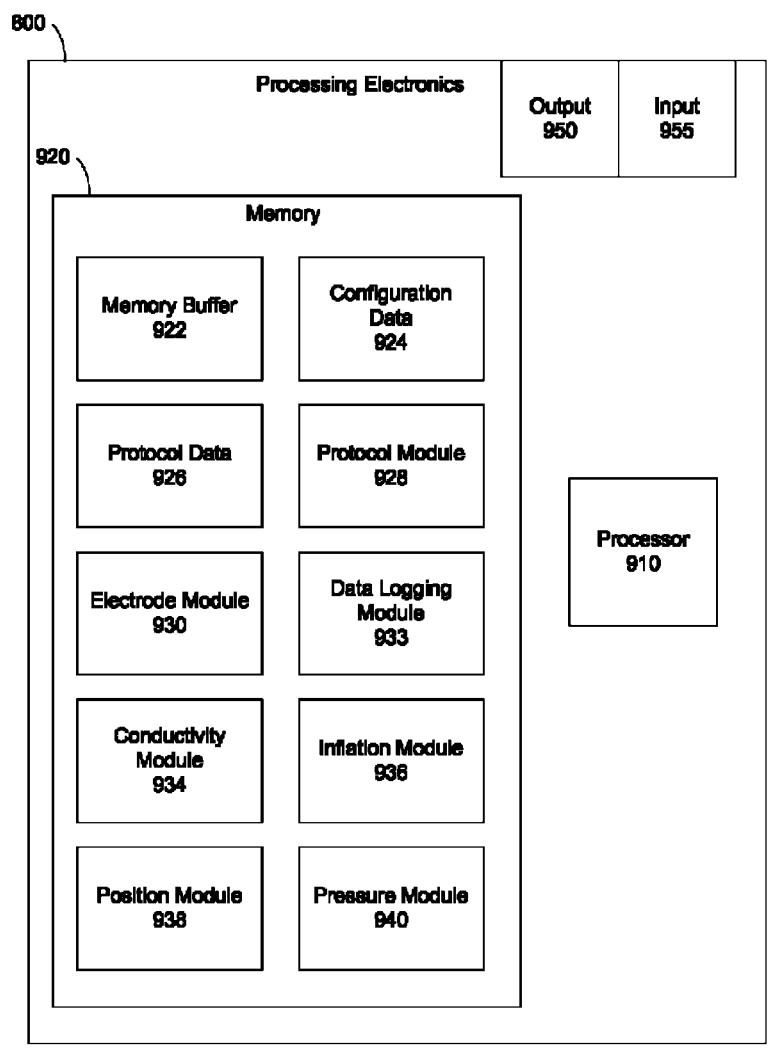
FIG. 9 is a schematic block diagram of the processing electronics of the device of FIG. 1, shown according to an exemplary embodiment.

Referring to FIG. 9, a detailed block diagram of processing electronics 800 of FIG. 8 is shown, according to an exemplary embodiment. Processing electronics 800 includes a processor 910 and a memory 920. According to an exemplary embodiment, processor 910 is configured to execute computer code stored in memory 920 to complete and facilitate the activities described herein. For example, memory 920 is shown to include modules 922-940 which are computer code modules (e.g., executable code, object code, source code, script code, machine code, etc.) configured for execution by processor 910. When executed by processor 910, processing electronics 800 is configured to complete the activities described herein. Processing electronics includes hardware circuitry for supporting the execution of the computer code of modules 922-940. For example, processing electronics 800 includes hardware interfaces (e.g., output 950) for communicating control signals (e.g., analog, digital) from processing electronics 800 to circuit 806. Processing electronics 800 may also include an input 955 for receiving, for example, sensor data from circuit 806, response information from circuit 806, user inputs from control inputs 704, or for receiving data or signals from other systems or devices. According to various embodiments, processor 910 may be or include one or more microprocessors, an application specific integrated circuit (ASIC), a circuit containing one or more processing components, a group of distributed processing components, circuitry for supporting a microprocessor, or other hardware configured for processing. Memory 920 can be any volatile or non-volatile memory device capable of storing data or computer code relating to the activities described herein.

Memory 920 includes a memory buffer 922 for receiving sensor data, for example response information, pressure data, voltage data, capacitive sensing data, conductivity data, etc. The sensor data may be stored in memory buffer 922 until buffer 922 is accessed for data. For example, a protocol module 928, electrode module 930, data logging module 932, conductivity module 934, inflation module 936, position module 938, pressure module 940, or another process that uses sensor data may access buffer 922. The sensor data stored in memory 920 may be stored according to a variety of schemes or formats. For example, the sensor data may be stored as streaming data, peak values, synchronous, asynchronous, separate buffers for each data type, one buffer for all sensor data, or any other suitable format for storing sensor information.

Memory 920 further includes configuration data 924. Configuration data 924 includes data relating to device 100, such as electrode information that the electrode module 930 can interpret to determine how to command the electrodes 128 to cause a muscle contraction, for example the number of electrodes, electrode conductivity, conductivity as a function of expansion or pressure, etc. According to another embodiment, configuration data 924 may include response information configuration data which the protocol module 928 and/or data logging module 932 can interpret to determine if response information will include an electrical signal received from at least one of the electrodes 128, a pressure signal received from a pressure sensor 520, or both. According to another embodiment, configuration data 924 may include pump information, such as whether the pump 510 is hand-operated or motorized, and control information of the motorized pump. According to another embodiment, configuration data 924 may include sensor information, such as the existence, location, and calibration of pressure sensors 520, conductivity sensors, capacitive sensors, and the like.

Memory 920 further includes a protocol data 926 which includes data relating to the treatment protocol. Protocol data 926 may include data that protocol module 928 can interpret to determine how to command the electrical signal sent to electrodes 128. For example, protocol data 926 may include data relating to current, voltage, frequency, number of phases of stimulation signal, duration and pattern of stimulation periods, duration and pattern of rest periods, and/or duration of treatment. Protocol data 926 may include data relating to a predetermined pressure (e.g., prescribed pressure, target pressure, threshold pressure, etc.) for balloon 124. Protocol data 926 may be stored in memory 920 by the user or another (e.g., a health care professional).

Memory 920 further includes a protocol module 928 which includes logic for using configuration data 924, protocol data 926, sensor data from the memory buffer 922, and/or data received from another module to carry out the treatment protocol, e.g., providing stimulation commands to electrode module 930. Protocol module 928 may output data to data logging module 932 for recording, may cause outputs for providing an indication to a user, and may cause an output requesting a user to perform an activity (e.g., inserting probe 120, pressurizing balloon 124, forcing a contraction, etc.). Protocol module 928 may include logic to cause closed-loop control of the electrical stimulation based on response information received from memory buffer 922, electrode module 930, conductivity module 934, and/or pressure module 940.

Memory 920 further includes an electrode module 930 which includes logic for causing a contraction of a muscle in communication with electrode 128. Electrode module 930 may control the stimulation of a muscle in communication with electrodes 128 based on conductivity information received from conductivity module 934, position information received from position module 938, and/or pressure information received from pressure module 940. Electrode module 930 may include logic to control the current or voltage provided by electrodes 128 as a function of frequency, or to control the frequency in response to the current or voltage. According to an exemplary embodiment, electrode module 930 may include logic to use an 8-bit register to control the frequency, current, or voltage of the stimulation. Using an 8-bit register provides fine resolution for precise incontinence treatment.

Memory 920 further includes a data logging module 932 which includes logic for causing a response information to be recorded. Data logging module 932 may include logic for storing baseline information. Data logging module 932 may record processed information or may record raw sensor information, may record data directly from protocol module 928, may record data from memory buffer 922 or another module, and/or may record frequency and duration of use information. Recording frequency and duration of use information may provide a record of whether a patient is adhering to a protocol and complying with a daily usage and time regimen.

Memory 920 is shown to include a conductivity module 934 which includes logic for determining the conductivity of the environment of probe 120, balloon 124, and/or electrodes 128. Conductivity of the environment is dependent on many factors. For example, conductivity may depend on the conductivity and quantity of artificial lubricants used, the quantity of vaginal fluid present, which may change from day to day or during the treatment protocol, and/or the expansion of electrodes 128. Conductivity module 934 may receive sensor data directly or through memory buffer 922. Conductivity module 934 may provide conductivity information to electrode module 930, data logging module 932, or any other module requiring conductivity information.

Memory 920 is shown to include an inflation module 936 which includes logic for providing an indication to a user that the pressure inside balloon 124 has reached a predetermined value. According to one embodiment, the predetermined value is a pressure stored in protocol data 926. Inflation module 936 may use sensor data from memory buffer 922 or pressure information from pressure module 940. Inflation module 936 may include logic for causing inflation of balloon 124. For example, inflation module 936 may cause a request for a user to actuate pump 510 or may cause actuation of a motorized pump 510. Inflation module 936 may control pump 510 using configuration data 924 and pressure data received from memory buffer 922 or pressure module 940.

Memory 920 is shown to include a position module 938 which includes logic for determining if probe 120 is inserted and/or properly positioned. According to one embodiment, position module 938 may receive capacitive sensor data from memory buffer 922. According to an alternative embodiment, position module 938 may determine insertion of probe 120 from a change in continuity or a change in resistance between electrodes 128. According to another alternative embodiment, position module 938 may request user confirmation that probe 120 and/or balloon 124 are inserted, for example, by providing input via control inputs 704 on controller 104. Position module 938 may cause output from electrode module 930 to be inhibited if position module 938 determines that balloon 124 has been removed from the vagina. For example, position module 938 may cause electrodes 128 to stop providing an electric signal, or position module 938 may provide position information to protocol module 928 or to electrode module 930.

Memory 920 further includes a pressure module 940 which includes logic for determining the pressure inside balloon 124. Pressure module 940 may use configuration data 924, pressure data received directly from pressure sensor 520, or pressure data received from memory buffer 922. Pressure module 940 may provide pressure information to inflation module 936 and protocol module 928. Pressure module 940 may provide pressure information to electrode module 930, or may inhibit processing electronics 800 from causing a contraction of the muscle if the pressure in balloon 124 is below a threshold value, e.g., balloon 124 has not been sufficiently inflated. Pressure module 940 may receive response information from pressure sensor 520.

Figure 10:
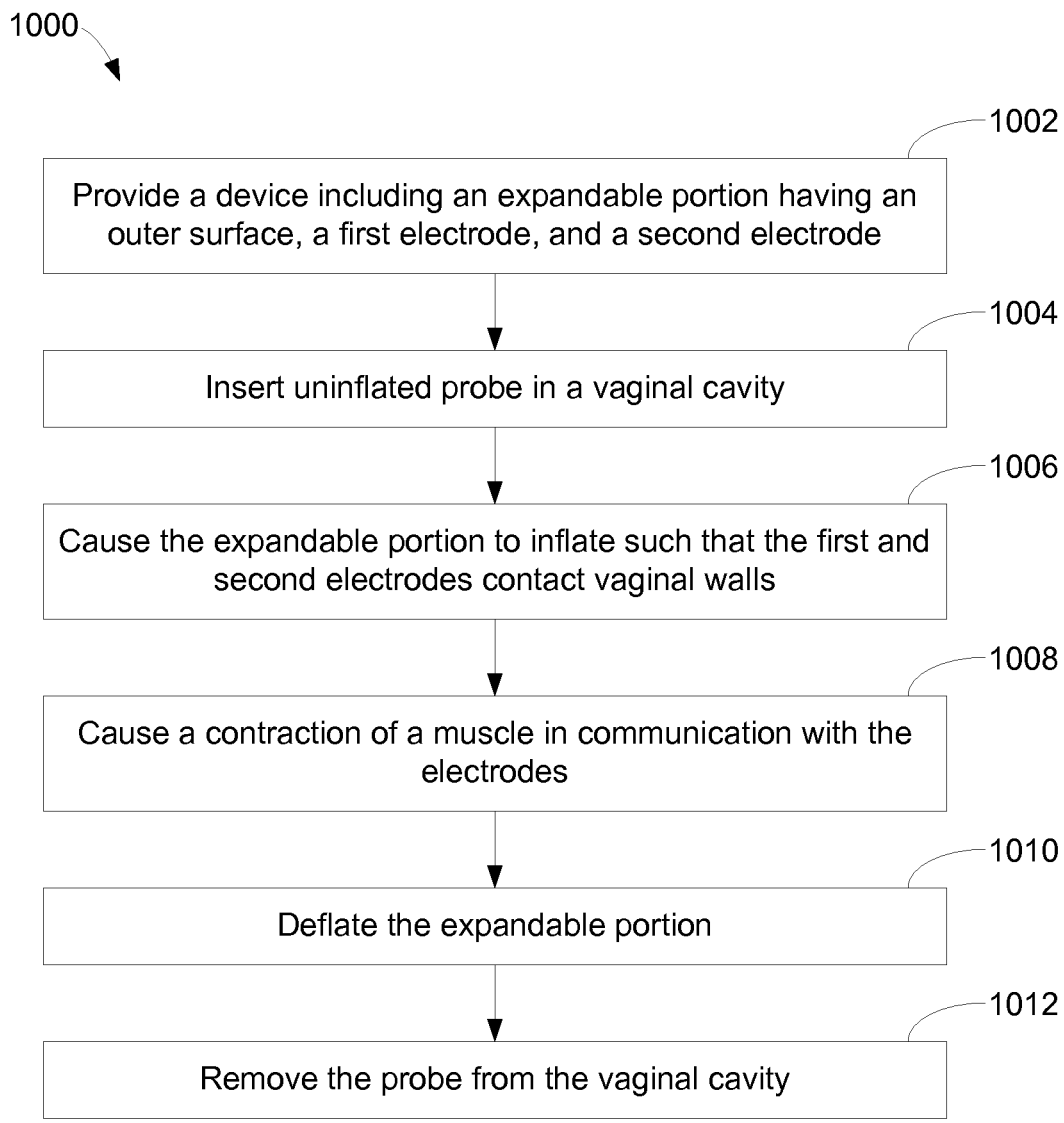
FIG. 10 is a schematic flow chart of a process for treating urinary incontinence, shown according to an exemplary embodiment.

Referring to FIG. 10, a flowchart of a process 1000 for treating urinary incontinence is shown according to an exemplary embodiment. Process 1000 is shown to include the steps of providing a device as described above and including an expandable portion having an outer surface, a first electrode, and a second electrode (step 1002). Process 1000 further includes the steps of inserting the uninflated probe in a vaginal cavity (step 1004), causing the expandable portion to inflate such that the first and second electrodes contact vaginal walls (step 1006), and causing a contraction of the muscle in communication with the electrodes (step 1008). Process 1000 further includes deflating the expandable portion (step 1010) and removing the probe from the vaginal cavity (step 1012). According to one embodiment, the first and second electrodes couple to the outer surface of the expandable portion and are configured to cause a contraction of a muscle and communication with the electrodes.

Figure 11:
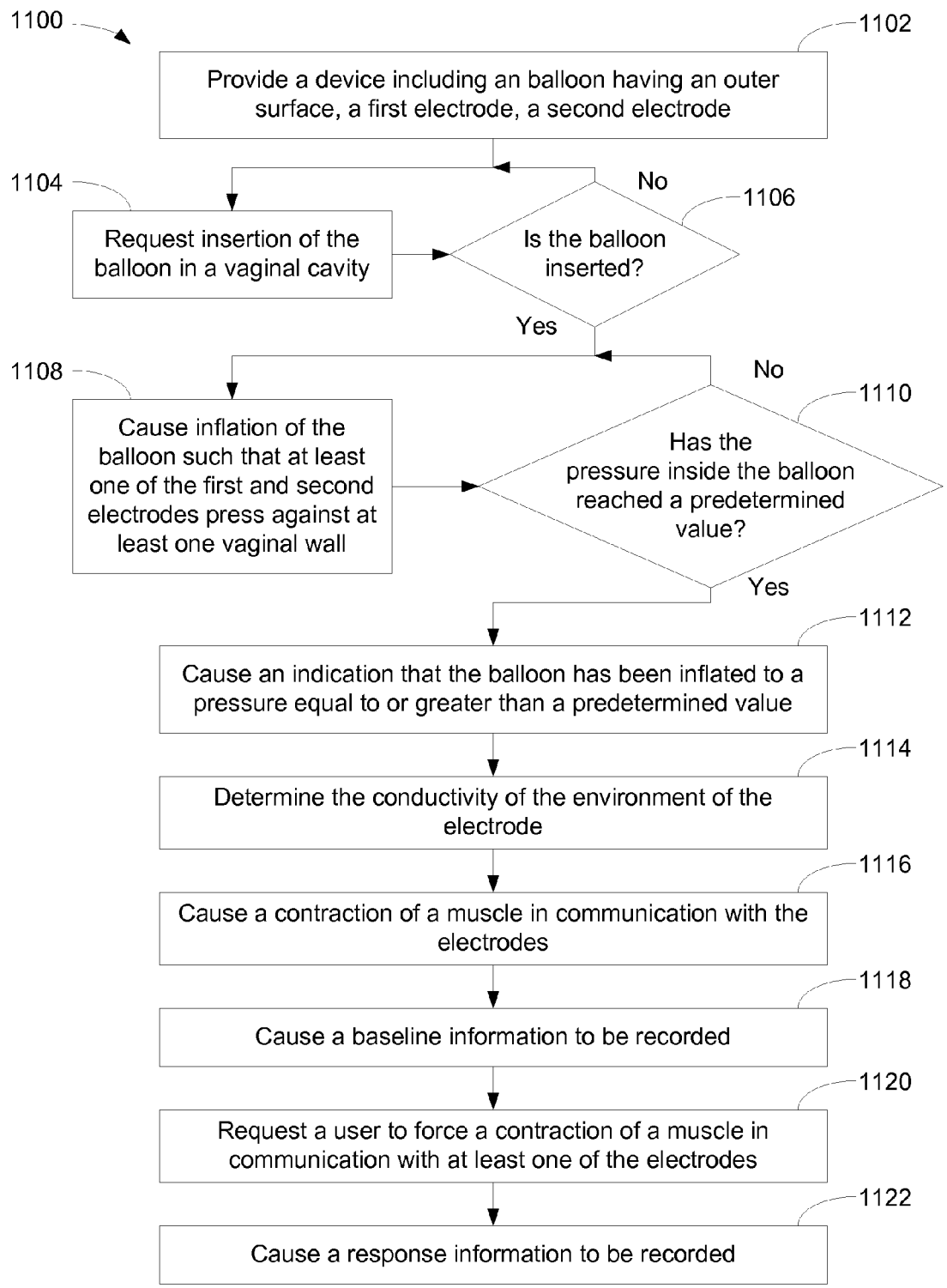
FIG. 11 is a schematic flow chart of a process for treating urinary incontinence, shown according to another exemplary embodiment.

Referring to FIG. 11, a flowchart of process 1100 for treating urinary incontinence is shown according to an exemplary embodiment. Process 1100 is shown to include the steps of providing a device as described above and including a balloon having an outer surface, a first electrode, and a second electrode (step 1102). Process 1100 further includes the step of requesting insertion of the balloon into a vaginal cavity (step 1104), for example, by indicating that device 100 is initialized and ready for insertion (e.g., illuminating in indicator lamp 712), providing an aural request through speaker 714, or providing instructions along with providing probe assembly 102. The determination of insertion may be an inference by processing electronics 800 (e.g., by position module 938) or by a confirmation from a user through control inputs 704. If the balloon is not inserted (step 1106) then process 1100 returns to step 1104. According to an alternate embodiment, if the balloon is not inserted, then step 1106 may return to itself waiting for determination that the balloon has been inserted (e.g., dwelling).

If the balloon has been inserted (step 1106), process 1100 causes inflation of the balloon such that at least one of the first and second electrodes press against at least one vaginal wall (step 1108). According to various embodiments, step 1108 may include requesting a user to actuate pump 510, causing actuation of pump 510, and/or causing operation of a motorized pump. If the pressure inside the balloon has not reached a predetermined value (step 1110) then process 1100 returns to step 1108. Alternatively, if the pressure inside the balloon has not reached a predetermined value within a threshold time, process 1100 may proceed to an error process (not shown) which may cause an indication of error. If the pressure inside the balloon has reached a predetermined value (step 1110), then process 1100 causes an indication that the balloon has been inflated to a pressure equal to or greater than a predetermined value (step 1112). According to various embodiments the indication may be visual, aural, or haptic. Process 1100 may further include the step of determining the conductivity of the environment of the electrode (step 1114). For example, a conductivity sensor in probe 120 may determine the effects of vaginal fluids or lubricants have on the conductivity of the probe environment. The conductivity sensor may measure the resistivity between electrodes 128 or measure the current delivered for a provided voltage. According to one embodiment, a low voltage (e.g., 2 Volts) is provided across electrodes 128, the resulting current is measured, and resistance is calculated.

Process 1100 is further shown to include the steps of causing a contraction of a muscle in communication with the electrodes (step 1116) and causing a baseline information to be recorded (step 1118). Baseline information may be information from sensors 802 measured at a point in time after the balloon has been inserted and the pressure in the balloon has reached a threshold value and no current or voltage is passing through electrodes 128. Process 1100 is further shown to include the steps of requesting a user to manually or volitionally force a contraction of a muscle in communication with at least one of the electrodes (step 1120) and causing a response information to be recorded (step 1122). Steps 1120 and 1122 enable tracking of the user's progress. The recorded data may be provided to a healthcare professional or reviewed by the user. Providing data to a healthcare professional may include reviewing data directly from display 710 on controller 104, uploading the data from controller 104 to a computer, or transmitting the response information across the Internet to a computer (e.g., a server).

Various alternate embodiments of the process described are contemplated. For example, the order of steps may be changed, e.g., determining if the balloon is inserted (step 1106) may be a prerequisite to, or occur simultaneously with, determining the conductivity of the environment of the electrode (step 1114). According to another embodiment, causing a baseline information to be recorded (step 1118) may occur before causing a contraction of the muscle in communication with the electrodes (step 1116). Process 1100 may not include all of the steps listed. For example, process 1100 may not include the steps of requesting insertion of the balloon into a vagina (step 1104) or determining if the balloon has been inserted (step 1106). According to another embodiment, process 1100 does not include the step of determining the conductivity of the environment of the electrode (step 1114). According to various other embodiments, process 1100 may not include the steps of causing a baseline information be recorded (step 1118), requesting a user to force a contraction of a muscle in communication with at least one of the electrodes (step 1120), or causing a response information to be recorded (step 1122). Process 1100 may include additional steps, e.g., lubricating the balloon, inserting the uninflated balloon in a vaginal cavity, deflating the balloon, and/or removing the balloon from the vaginal cavity.

According to another embodiment, process 1100 may output an indication of the response information, for example, a outputting a value corresponding to the strength of the force contraction by illuminating a portion of the sequential lamps 708, displaying a pressure, and/or displaying a normalized strength value, e.g., on a 1-10 scale.

Figure 12:
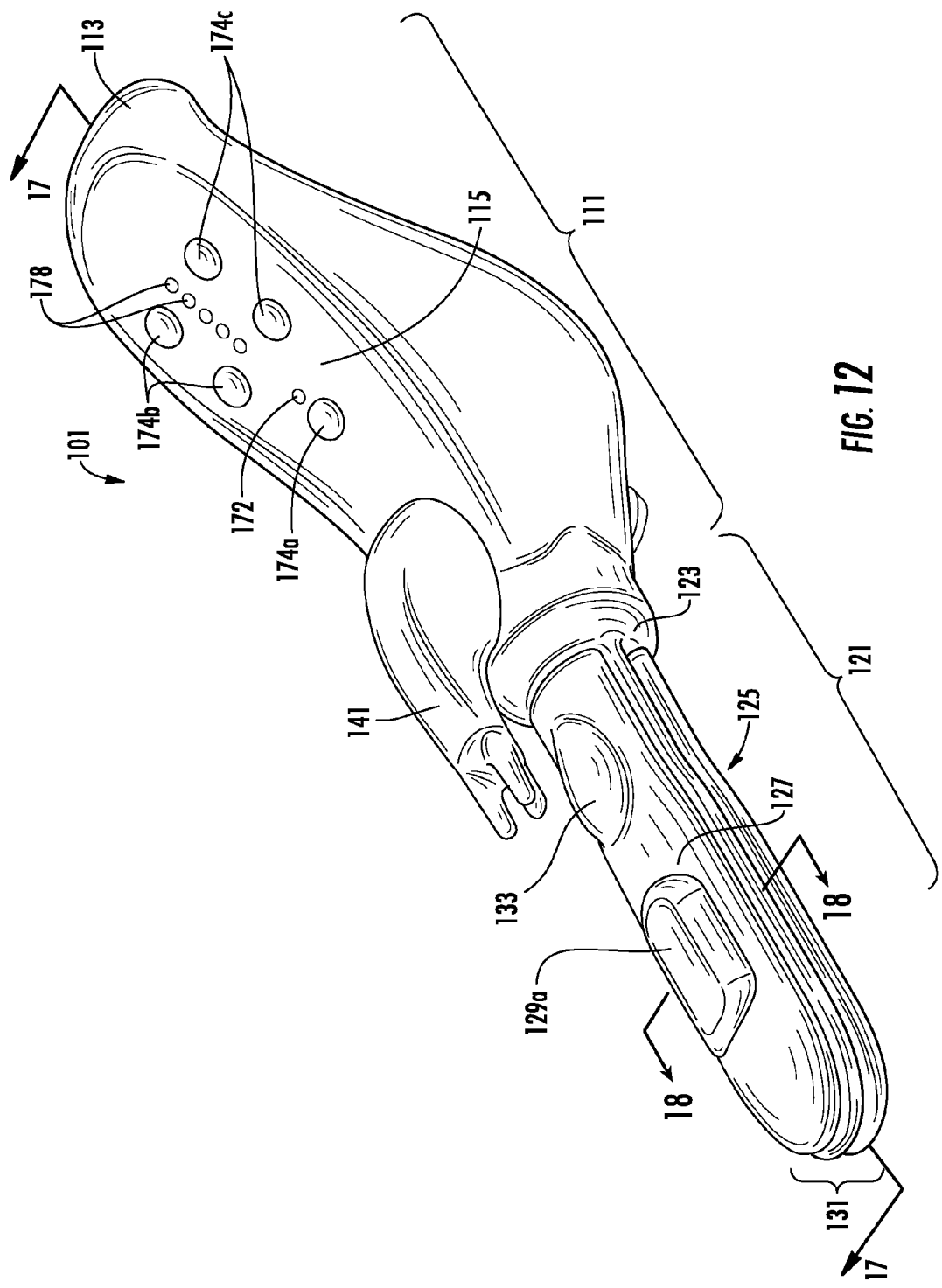
FIG. 12 is a perspective view of a stimulation device, shown according to an exemplary embodiment.

Referring to FIG. 12, a perspective view of a device 101 is shown according to an exemplary embodiment. As described below, device 101 may be used for causing a pleasurable sensation or toning pelvic floor muscles, specifically in women. According to the exemplary embodiment shown, device 101 includes a housing, shown as handle 111, and a probe 121. Handle 111 provides the user a region which may be grasped for control and manipulation of the device 101 and to facilitate insertion, positioning, and removal of probe 121. Handle 111 is shown to include a sleeve 113 configured to cover the majority of handle 111. Sleeve 113 is preferably pliable and provides a smooth and watertight surface to handle 111 wherein the smooth and watertight surface facilitates cleaning which is beneficial due to the handle's 111 proximity to bodily fluids and the vaginal opening during use. Sleeve 113 may also be translucent to allow lights 172, 178 (e.g., lamps, LEDs, displays, etc.) or a display (not shown) on handle 111 to shine through. Sleeve 113 allows actuation of control inputs, shown as buttons 174, located below sleeve 113. Further, sleeve 113 may be customizable, e.g., bearing various colors or logos. Preferably, sleeve 113 is formed from silicone rubber.

According to the exemplary embodiment, handle 111 includes a first portion, shown as interface 115, which includes a plurality of control inputs (e.g. toggles, switches, an electro-acoustic transducer configured to receive voice commands, a touch sensitive display, etc.), shown as buttons 174, configured to enable user input into device 101. For example, button 174a may be a power button configured to turn device 101 on and off. Button 174a may be a combination power/mode button configured to turn device 101 on and off and to switch between operating states (e.g., vibrational patterns, pleasurable sensation versus muscle toning, etc.). According to the exemplary embodiment, buttons 174b control the frequency or speed of vibration, and buttons 174c increase or decrease the intensity of the electrical stimulation. According to an alternate embodiments, buttons 174 may provide other control inputs, for example, stimulation select, pressure select, increase, decrease, frequency, amplitude, current, voltage, pause, etc.

According to the embodiment shown, interface 115 includes a plurality of sequentially oriented lamps 178 (e.g., lights, LEDs, etc.) configured to indicate the level of electrical stimulation intensity. According to other embodiments, lamps 178 may indicate a level of vibrational intensity or the pressure inside balloon 125. Interface 115 may also include a display (not shown) configured to numerically indicate balloon pressure, stimulation intensity, or vibrational intensity. The display may be further configured to display images, pictures, or videos (e.g., instructional or erotic images), or to display a waveform representative of the stimulation signal. The display and the plurality of lamps 178 may indicate the same or different information. Interface 115 may include a plurality of indicator lamps 172 (e.g. lights, LEDs, etc.) which may indicate a power state (e.g., power on, battery low, etc.), a communication state (e.g., communication to a computer, etc.), pressure state (e.g., the pressure inside balloon 125 has reached a predetermined value), an error state, etc.

According to an alternate embodiment, interface 115 may be located on a separate control unit. The control unit may be coupled to handle 111 via cable 106 or configured to communicate with device 101 wirelessly, for example, using Bluetooth, wireless local area network, or personal area network protocols. According to various alternate embodiments, any or all of the components of device 101 may be located on or in the control unit. For example, lamps 172, 178, control inputs 174, and/or power supply 809 (e.g., batteries) may be located on the control unit. Alternatively, display 811, audio device 813, processing electronics 801, and probe controller circuit 807 may be located in the control unit. According to another embodiment, pump 511 may be located in controller 104.

According to the embodiment shown, probe 121 generally has the form of an elongated cylinder having an open proximal end and a closed distal end. Probe 121 may include a neck portion 123 near the proximal end. Probe 121 includes a member or expandable portion, shown as balloon 125. According to the exemplary embodiment, balloon 125 includes a single inflatable balloon having an outer surface 127. According to alternate embodiments, the expandable portion may include a plurality of balloons. According to various embodiments, the plurality of balloons may be oriented axially, radially, circumferentially, or some combination thereof. Balloon 125 may be formed of an airtight, elastic, biocompatible material, such as silicone rubber. According to alternate embodiments, balloon 125 may be formed of any suitable material.

Figure 13:
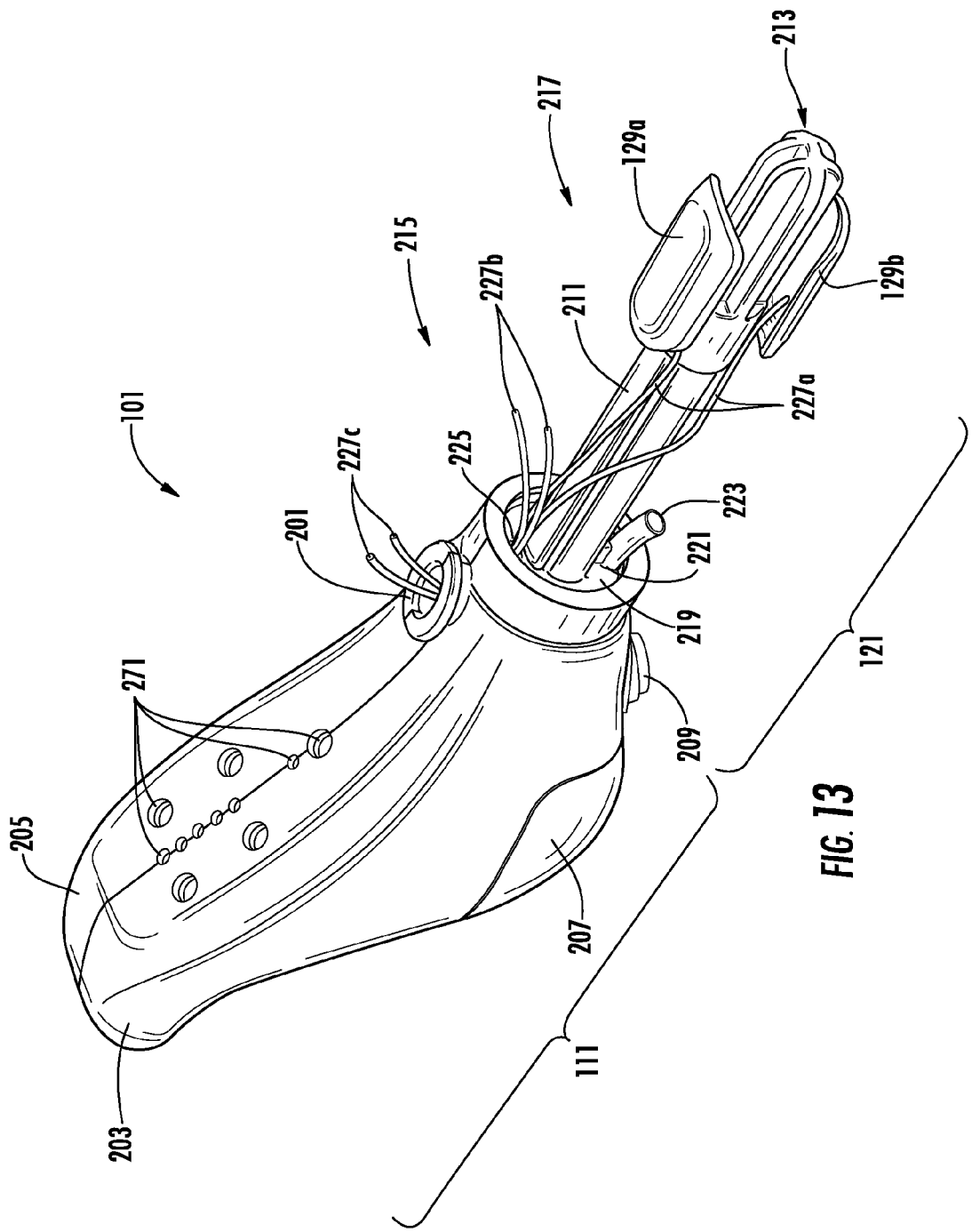
FIG. 13 is a perspective view of a portion of the device of FIG. 12, shown according to an exemplary embodiment.

Probe 121 is further shown to include at least one electrode 129, shown as electrode 129a (e.g., first electrode, top electrode, etc.). Preferably, electrode 129 is mounted to outer surface 127 of balloon 125 in such a manner that electrode 129 may come into contact with tissue adjacent to balloon 125 when probe 121 is in an inserted position. Referring briefly to FIG. 13, probe 121 may include a second electrode 129b (e.g., bottom electrode, etc.). First electrode 129a and second electrode 129b are shown radially opposite one another; however, probe 121 may have a plurality of electrodes 129, the plurality of electrodes being located anywhere on probe 121, e.g., left and right sides, both on top, axially or circumferentially offset, or equally or unequally spaced circumferentially around probe 121. The relative position of the electrodes 129 is dependent upon the particular tissue to receive the electrical stimulation. The placement and relative spacing of the electrodes will determine, in part, the effectiveness of the muscle contraction as a result of the electrical stimulation. According to various embodiments, a plurality of electrodes 129 may be energized at the same time, different electrodes (e.g., a subset of a plurality of electrodes) may be actuated during different phases of an exercise or pleasurable sensation session, or different electrodes may be actuated during different sessions. For example, an even number of electrodes 129 may be actuated in pairs, or an odd number of electrodes may be actuated in a rotating pattern. Actuating different electrodes 129 at different times may cause different muscles to contract, thereby toning more and different pelvic floor muscles and preventing the muscles from becoming adjusted or de-sensitized to the electrical stimulation. According to various embodiments, a user may select which electrodes 129 are actuated or may select a pattern or actuation of electrodes in order to provide a desired pleasurable sensation. Alternatively, position of electrodes 129 may be chosen to facilitate manufacture of balloon 125, for example, aligning electrodes 129 with G-Spot stimulator 133 may simplify mold design. The plurality of electrodes 129 may have the same or different shape. Electrode 129 is configured to deliver electrical pulses (e.g., signals, currents, voltages, frequencies, etc.) to stimulate muscle contraction to strengthen the muscles in the area of the pelvic floor. It is contemplated that the electrical stimulation provided to tone pelvic floor muscles may be different than the optimal stimulation to provide a pleasurable sensation. Electrode 129 may also communicate a response information (e.g., a signal indicative of the contractive force of the muscles) to processing electronics 801. According to one embodiment, the response information is a voltage created by the contracting muscle. According to another embodiment, the response information is an electric potential difference between first electrode 129a and second electrode 129b. The muscle contraction causing the response information may be caused by electrode stimulation of the muscle or may be the result of a manual contraction caused by the user.

According to the exemplary embodiment, electrodes 129 may be formed from stainless steel, and in another embodiment, the electrodes may be formed from an expandable, conductive silicone rubber or any other suitable material. It may be desirable to limit electrodes 129 from expanding so as to maintain a relatively consistent conductivity or to prevent the muscle stimulation from moving as balloon 125 is expanded. Further, electrodes formed of materials different than balloon 125 may not expand at the same rate as balloon 125 during inflation. Therefore, it may be beneficial to provide a balloon 125 which expands non-uniformly.

According to the exemplary embodiment, electrode 129a is supported by a first portion of balloon 125. The first portion of balloon 125 and a second portion of balloon 125 cooperate to cause balloon 125 to expand in a radially and/or circumferentially non-uniform manner relative to probe 121. Similarly, electrode 129b is supported by a third portion of balloon 125. The first and third portions of balloon 125 cooperate to cause balloon 125 to expand in a radially and/or circumferentially non-uniform manner relative to probe 121. Non-uniform expansion of balloon 125 may cause balloon 125 to substantially contour to the anatomy of a user, for example, to conform to the contours of the user's vagina. Non-uniform expansion of balloon 125 may also facilitate a suitable and comfortable fit of balloon 125 for the user.

Figure 17:
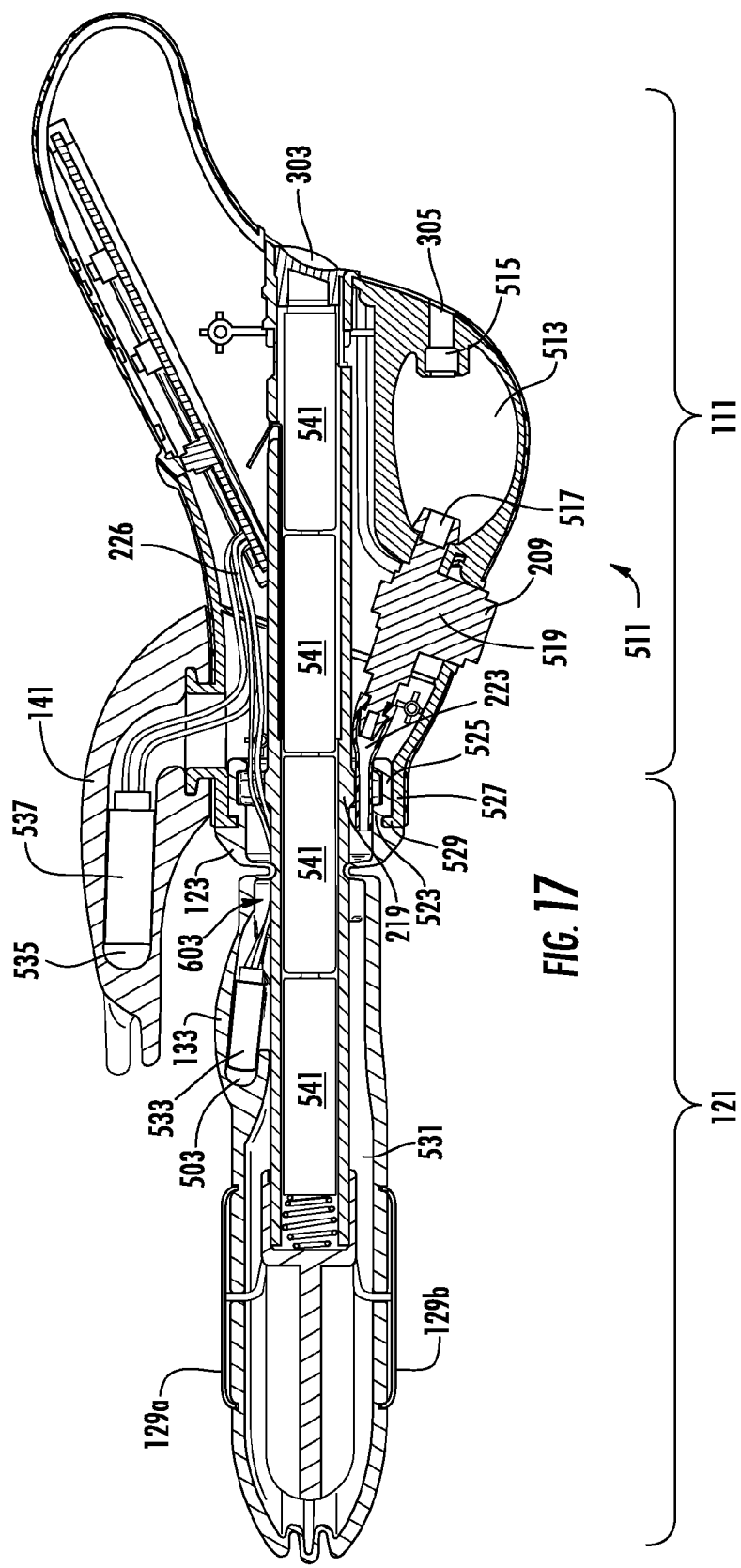
FIG. 17 is a longitudinal cross-section view of the device taken along line 17-17 of FIG. 1, shown according to an exemplary embodiment.
Figure 18A:
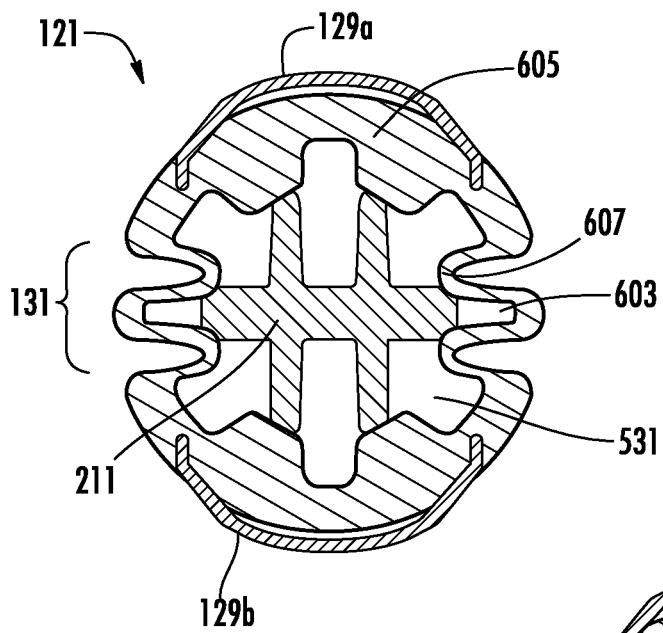
FIG. 18A is a radial cross-section view of the device taken along line 18-18 of FIG. 1 in a deflated state, shown according to an exemplary embodiment.

According to one embodiment, the second portion may be an expansion portion (e.g., folds, pleats, articulation, etc.), shown as bellows 131. The folds of bellows 131 provide a region of increased surface area of balloon 125 in the deflated state, which allows balloon 125 to expand in a circumferentially non-uniform manner. As shown, bellows 131 extend longitudinally or axially along the sides of balloon 125. Bellows 131 are further shown to extend around the distal end of balloon 125. Accordingly, bellows 131 are shown to extend substantially continuously around the midsection (e.g. equatorially region) of balloon 125. According to various alternate embodiments, bellows 131 may extend discontinuously, in a top/bottom meridian formation, or in any suitable orientation to cause differential expansion of balloon 125. Probe 121 may include any number of bellows 131 equally or unequally spaced around probe 121. Referring briefly to FIGS. 17 and 18A, bellows 131 may be configured to provide an opening 603 through which wires 227 may pass when balloon 125 is in a deflated state. According to the exemplary embodiment, bellows 131 are configured such that a majority of the expansion of balloon 125 occurs in the bellows region.

Figure 18B:
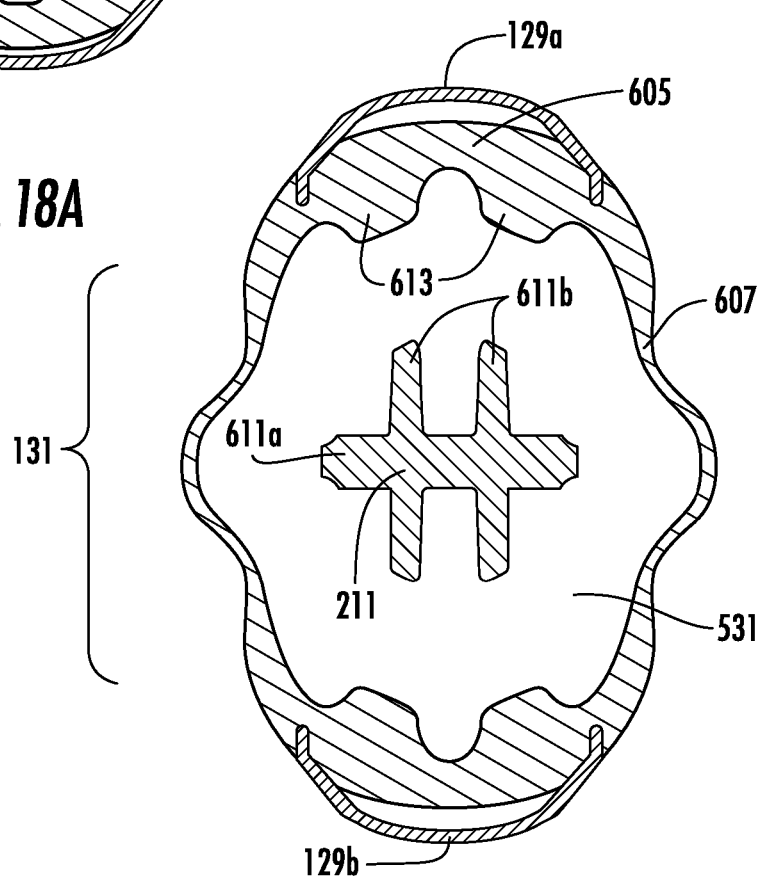
FIG. 18B is a radial cross-section view of the device taken along line 18-18 of FIG. 1 but showing the device in an inflated state, according to an exemplary embodiment.

Referring now to FIG. 18A, a radial cross-section of probe 121 is shown in a first state (e.g., minimum expansion, contracted, deflated, etc.), whereas FIG. 18B shows a radial cross-section of probe 121 in a second state (e.g., expanded state, inflated, etc.). As seen in the first, deflated state, bellows 131, first and third portions of balloon 125 are closely adjacent to or abut shaft 211. However, in the second, or expanded state, bellows 131 have substantially unfolded allowing radial expansion of the first and third portions of balloon 125 and electrodes 129a and 129b provided thereon.

According to another embodiment, the first portion of balloon 125 may have a first thickness 605, and the second portion of balloon 125 may have a second thickness 607, specifically thickness 605 of the first portion being greater than thickness 607 of the second portion. Accordingly, the first portion tends to resist circumferential expansion and maintain its form when balloon 125 is inflated. The second portion provides a "path of least resistance" for expansion, such that for a prescribed level of inflation pressure, balloon 125 will stretch or expand the material of balloon 125 more in the second region than in the first region.

According to one embodiment, at minimum expansion, balloon 125 has a diameter of between approximately 1 inch and approximately 2 inches. Preferably, at minimum expansion, balloon 125 has a diameter of approximately 1⅛ inches. According to one embodiment, at maximum expansion, balloon 125 has a diameter of between approximately 2 inches and approximately 4 inches, the preferred maximum expansion of balloon 125 being between approximately 3 inches and approximately 4 inches in diameter. Expansion of balloon 125 in these ranges enables contouring balloon 125 to women of different anatomical sizes.

Referring to FIGS. 12, 13, and 17, device 101 is shown to have a first vibrating element, shown as a Gräfenberg Spot or G-Spot stimulator 133, and a second vibrating element, shown as a clitoral stimulator 141. Clitoral stimulator 141 is in the shape of a curved projection or finger which extends outwardly from the outer surface 127 of balloon 125 adjacent neck 123 of balloon 125. As shown in the figures, the projection curves in the distal direction (i.e., away from neck 123 of balloon 125). G-Spot stimulator 133 is shown as a rounded projection or "bump." G-Spot stimulator 133 extends a shorter distance outwardly from the surface of balloon 125 than clitoral stimulator 141 such that the height of clitoral stimulator 141 is greater than the height of G-Spot stimulator 133. G-Spot stimulator 133 is located between distal end 213 of balloon 125 and clitoral stimulator 141, and clitoral stimulator 141 is located between G-Spot stimulator 133 and the proximal end of the balloon. G-Spot stimulator 133 may be used to indicate to a user that probe 121 is properly inserted. For example, G-Spot stimulator 133 may provide a user a point of reference for internal positioning probe 121.

In the exemplary embodiment shown, G-Spot stimulator 133 includes a cavity 503 and clitoral stimulator 141 includes a cavity 535. Cavities 503 and 535 are configured to receive vibration actuators 533 and 537, respectively, which are configured to cause vibration of the associated stimulator. According to an alternate embodiment, cavities 503 and 537 may be configured to receive a sensor (e.g., capacitive sensor, pressure sensor, conductivity sensor, etc.), which will be discussed further below. In another embodiment, electrodes 129 may be positioned along the outer surfaces of G-Spot stimulator 133 and clitoral stimulator 141. In another embodiment, device 101 may include a single actuator that generates vibrations which are transmitted to balloon 125, G-Spot stimulator 133 and clitoral stimulator 141.

The first vibrating element is shown coupled or mounted just below the outer surface 127 of balloon 125 near proximal end 215 of balloon 125. Thus, in this embodiment, the material that forms the outer surfaces of the first vibrating element is integral or continuous with the material of balloon 125. The second vibrating element is shown coupled or mounted to flange 201 on handle 111 and is discontinuous with the material of balloon 125. The material of balloon 125 and the outer surfaces of the first and second vibrating elements may be any stretchable or expandable biocompatible material, and in one embodiment may be silicone rubber.

Referring to FIG. 13, a perspective view of a portion of device 101 is shown with sleeve 113 and balloon 125 removed, according to an exemplary embodiment. Handle 111 may be formed of a plurality of portions, such as a "clam shell" assembly. As shown, handle 111 includes a left portion 203, a right portion 205, and a bottom portion 207, wherein left portion 203 and right portion 205 are hollow, substantially symmetric pieces of ABS plastic coupled together to form a housing. In the embodiment shown, left portion 203 and right portion 205 form a structure (e.g., base, support, etc.), shown as flange 201 which is configured to support clitoral stimulator 141 and to form a passage through which wires 227c may pass into handle 111. Bottom portion 207 may include an inflation device, wherein bottom portion 207 is formed of a deformable material, for example, a silicone rubber which is sufficiently pliable to compress the inflation device and to return to shape. According to various alternate embodiments, bottom portion 207 may be a rigid portion movably coupled to left portion 203 and/or right portion 205. Left portion 203, right portion 205, and bottom portion 207 may be formed of any suitable material, may be formed of the same or different materials, or may be formed as one element. Portions of handle 111 may be coupled by snap fit, fastener, hinge, and/or any other suitable coupling technique. Handle 111 is further shown to include a release valve 209, discussed in detail below, and a plurality of holes 271 configured to receive buttons 174 and lamps 172, 178.

According the exemplary embodiment seen in FIGS. 13 and 16-18B, device 101 includes a shaft 211 configured to house batteries used to power device 101 or components thereof. As shown, shaft 211 is an elongated structure having a distal end 213 and a proximal end 215, the proximal end 215 being coupled to handle 111. According to an alternate embodiment, shaft 211 may be interconnected to a remote control unit via a cable. Shaft 211 may include an operative region 217 located between proximal end 215 and distal end 213, the operative region 217 being configured to be substantially located within the vagina when probe 121 is in an inserted position. Shaft 211 may be solid, hollow, or any combination thereof.

As shown, shaft 211 includes a radially extending flange (e.g., collar), shown as bulkhead 219. Bulkhead 219 is configured to provide a substantially airtight seal between handle 111 and balloon 125. According to the exemplary embodiment, bulkhead 219 includes a first passage, shown as bottom passage 221, and a second passage, shown as top passage 225. Bottom passage 221 may be configured to allow a conduit, shown as tube 223, to extend from an inflation device into balloon 125. A substantially airtight seal is preferably formed (e.g., with silicone glue) between tube 223 and bulkhead 219. Top passage 225 may be configured to allow wires 227 to pass from electrodes 129 and/or other sensors or motors into handle 111. As shown, wires 227a couple to electrodes 129, and wires 227b couple to G-Spot vibration actuator 533. A substantially airtight seal may be formed (e.g., with silicone glue) between wires 227 and bulkhead 219. Bulkhead 219 may have any number of passages, and the passages may have any orientation around shaft 211. Alternatively, bulkhead 219 may include one passage for passing both tube 223 and wires 227.

According to alternate embodiments, tube 223 and/or wires 227 may be routed through shaft 211. Shaft 211 may include perforations configured to allow pressurizing fluid pumped through shaft 211 to enter into balloon 125. Routing pressurizing fluid, tube 223, and/or wires 227 through shaft 211 may eliminate the need for passages 221, 225 through bulkhead 219. Accordingly, these passages may be removed in order to improve the airtight seal between handle 111 and balloon 125.

Figure 15:
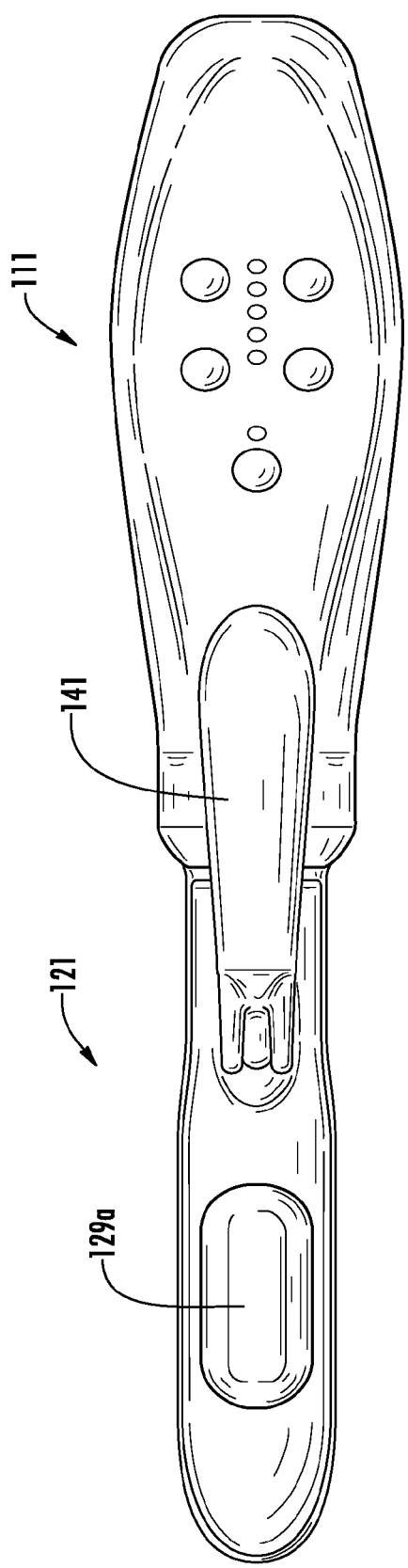
FIG. 15 is a top plan view of the device of FIG. 12, shown according to an exemplary embodiment.
Figure 14:
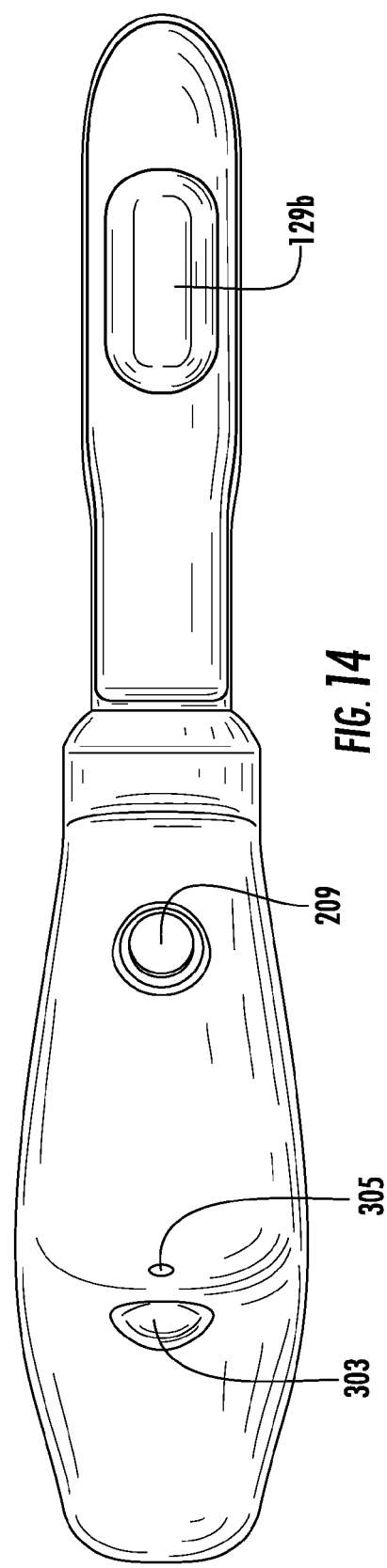
FIG. 14 is a bottom plan view of the device of FIG. 12, shown according to an exemplary embodiment.

Referring to FIGS. 14 and 15, a bottom view and a top view, respectively, of device 101 are shown according to an exemplary embodiment. Handle 111 includes a battery cap 303 configured to retain batteries 541 within shaft 211. As shown, battery cap 303 cap forms an end portion of shaft 211. According to alternate embodiments, battery cap 303 may be configured to allow wires 227 to pass out of handle 111, for example, to a power outlet or to a remote control unit. Handle 111 is further shown to include structure such as air inlet 305 (or orifice, valve, grommet, etc.) for inflation of balloon 125 described further below.

The diameter of balloon 125 may be substantially uniform over the length of probe 121, or the diameter of balloon 125 may vary. As shown, proximal end 215 of balloon 125 has a first diameter, and distal end of balloon 125 has a second diameter, the second diameter being greater than the first diameter. According to one embodiment, probe 121 transitions from the first diameter to the second diameter between neck portion 123 and electrode 129. According to the embodiment shown in FIGS. 3 and 5, balloon 125 begins to transition from the first diameter to the second diameter proximate G-Spot stimulator 133. Varying the diameter of balloon 125 along the length of probe 121 effects the expansion of balloon 125 along the length of probe 121. For example, the smaller proximal diameter limits expansion at proximal end 215 while allowing greater expansion of balloon 125 near electrodes 129 and proximal end 212, thereby contouring balloon 125 to the vaginal cavity. This further enables electrodes 129 to press against vaginal walls without applying excessive pressure on the introitus (vaginal entrance).

Figure 16:
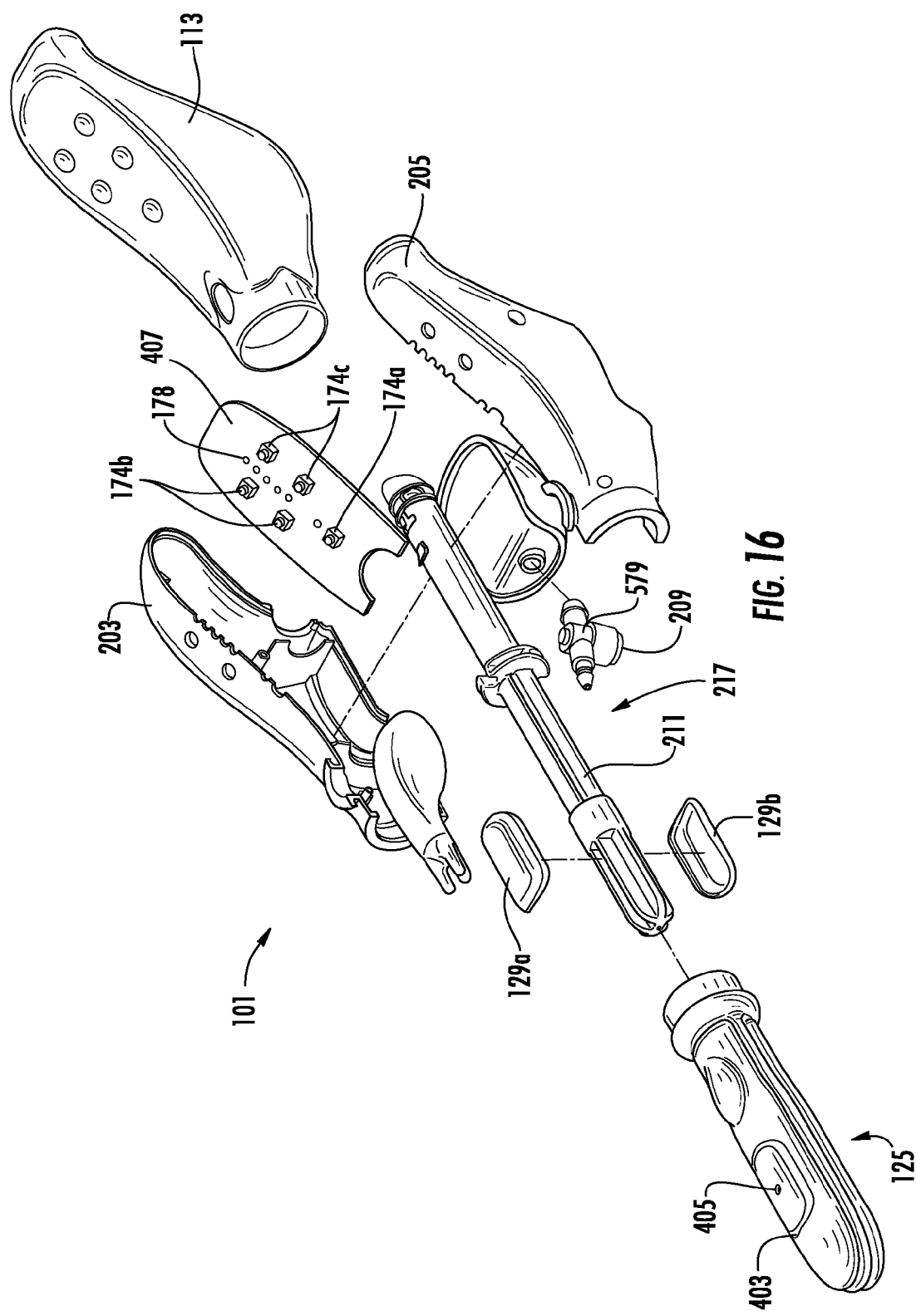
FIG. 16 is an exploded perspective view of a portion of the device of FIG. 12, shown according to an exemplary embodiment.

Referring to FIG. 16, a partially exploded view of device 101 is shown with tube 223 and wires 227 removed for clarity, according to an exemplary embodiment. As shown, balloon 125 includes a depression, cavity, or pocket 403 configured to receive electrode 129. According to an exemplary embodiment, a periphery of electrode 129 is configured to seat into pocket 403, and a sealant (e.g., silicone glue) may be used to couple electrode 129 to pocket 403 and to form a substantially airtight seal between electrode 129 and balloon 125. Forming a seal between an outer periphery of electrode 129 and balloon 125 achieves the added benefit of preventing fluid or debris from getting underneath electrode 129, thereby facilitating sanitary maintenance of probe 121. Balloon 125 is further shown to include an aperture, shown as hole 405, which is configured to permit passage of wires 227 from electrode 129 to the interior of balloon 125. A sealant may be used to retain wires 227 in place and to form a substantially airtight seal between wires 227 and balloon 125.

According to the embodiment shown, probe 121 comprises only one balloon 125 configured to surround operative region 217 of shaft 211. Referring briefly to FIG. 23, singular balloon 125 is shown to surround the entire portion of shaft 211 located within a vagina 21 when probe 121 is in an inserted position. FIG. 23 schematically depicts the embodiment of the device depicted and generally described in relation to FIGS. 1-11. However, it is to be understood that the embodiment of the device depicted and generally described in relation to FIGS. 12-22 would be similarly situated when in use. One key difference is that the vibration element 141 would extend to a point in which it abuts or is in contact with the clitoris or the surrounding tissue. According to various embodiments, probe 121 is in an inserted position when electrodes 129 are located within the vagina 21 or when G-Spot stimulator 133 is proximate a user's Gräfenberg Spot (G-Spot) 23. Use of a single balloon has the benefit of minimizing costs (assembly and material) while also simplifying the structure of the device.

According to the exemplary embodiment, device 101 includes a printed circuit board 407 configured to be supported by left portion 203 and right portion 205 of handle 111. As shown, circuit board 407 is configured to support lamps 172, 178, input controls 174, and processing electronic 801. A power supply 809 may be coupled to circuit board 407 and batteries 541.

Referring to FIG. 17, a longitudinal cross-section of device 101 is shown according to an exemplary embodiment. Balloon 125 is shown to define a lumen or cavity 531, and cavity 531 is configured to receive shaft 211. Balloon 125 is shown to circumferentially surround at least a portion of shaft 211.

Probe assembly 102 is shown to include an inflation device located at least partially within bottom portion 207 of handle 111 for selectively inflating and deflating balloon 125. According to an exemplary embodiment, the inflation device includes a pump 511 which may be manually operated. Pump 511 includes a cavity within bottom portion 207, shown as bladder 513, and a first check valve 515 is located between bladder 513 and air inlet 305. Check valve 515 permits air to enter bladder 513 through air inlet 305 from outside of device 101 and prevents air from exiting back through air inlet 305 when bladder 513 is compressed. A second check valve 517 is located between tee connector 519 and bladder 513. Check valve 517 permits air to enter tee connector 519 from bladder 513 and prevents air from back flowing into bladder 513, for example, when bladder 513 expands.

As shown, tee connector 519 couples bladder 513, release valve 209, and tube 223. Release valve 209 may be of any suitable mechanism to permit air under pressure to be selectively released from balloon 125, for example a thumbscrew or a pushbutton. Release valve 209 may also act as a relief valve to prevent over-pressurization of balloon 125. Tube 223 extends from an outlet of tee connector 519 through bulkhead 219 into probe 121. In operation, squeezing bottom portion 207 compresses bladder 513 and forces air through tee connector 519 and tube 223 into balloon 125. When the squeezing force exerted on bladder 513 is released, bladder 513 will resume its natural, inflated position as air is drawn into bladder 513 through check valve 515. Bladder 513 is squeezed and released repeatedly to force pressurized air into balloon 125. Increased pressure in balloon 125 eventually causes inflation of balloon 125, which in turn causes electrode 129 to contact a vaginal wall. According to one embodiment, the level of inflation of balloon 125 is controlled by a user and may be selected to ensure a suitable and comfortable fit between balloon 125 and the user's vagina. According to another embodiment, the preferred level of inflation is stored in memory 921 of processing electronics 801 described below. According to various alternate embodiments, the inflation device may include a motorized pump, the inflation device may be located in a remote control unit and pressurized air directed into balloon 125 through flexible tubing, and/or the inflation device may be located within probe 121. As described, the pressurizing fluid of the exemplary embodiment is air; however, any suitable pressurizing fluid may be used, for example, water, saline, oil, or other gases or liquids.

According to various alternate embodiments, device 101 includes a pressure sensor barometrically connected to balloon 125 and located in probe 121 (e.g., in cavity 503), in handle 111, or in the control unit. The pressure sensor may visually display an indication of a pressure inside balloon 125 on handle 111, for example, a gauge, a light, a digital display, etc. Providing an indication of pressure enables a user to determine a preferred pressure and to repeatably return to that pressure. The pressure sensor may be configured to communicate (via wires or wirelessly) pressure information to processing electronics 801. For example, the pressure sensor may generate a response information (e.g., a signal indicative of the rise in pressure caused by contractive force of the muscles on balloon 125) triggered by the electrical stimulation provided by electrodes 129 or by the user manually (e.g., consciously, volitionally, voluntarily, etc.) forcing a contraction of her pelvic floor muscles. Tracking response information enables a user to determine progress in pelvic floor muscle toning.

According to an exemplary embodiment, neck portion 123 of probe 121 includes an external annular groove 523 and an internal annular groove 525. Internal annular groove 525 is configured to fit over a radial periphery of bulkhead 219, and a sealant (e.g., silicone glue) may be used between internal annular groove 525 and bulkhead 219 to form a substantially airtight seal. Proximate bulkhead 219, left handle portion 203 and right handle portion 205 cooperate to form a substantially cylindrical portion 527 and an inwardly extending annular flange 529. Substantially cylindrical portion 527 fits over neck portion 123 of probe 121 and helps to hold internal annular groove 525 against bulkhead 219. Inwardly extending flange 529 fits into external annular groove 523 of probe 121. Accordingly, neck portion 123 and handle 111 are configured to prevent balloon 125 from slipping free of handle 111.

Referring to FIGS. 18A and 18B, shaft 211 is shown to be axially located within cavity 531 of probe 121. According to the exemplary embodiment, shaft 211 is configured to provide sufficient rigidity to probe 121 to facilitate insertion of probe 121 into a vagina. Shaft 211 may include a plurality of portions (e.g., members, structures, regions, webs, etc.), shown as ribs 611, configured to support balloon 125. Ribs 611a may support bellows 131 and inhibit bellows 131 from collapsing into cavity 531. Balloon 125 may include a plurality of structures (stiffeners, portions, etc.), shown as lugs 613, which are shown to rest on ribs 611b when balloon 125 is in a fully deflated state. Lugs 613 provide cushioning between shaft 211 and a user. Lugs 613 may also stiffen portions of balloon 125 underneath electrodes 129, thereby reducing flexure of balloon 125 in the area of the electrode. As shown, bellows 131, lugs 613 and ribs 611 are configured to cooperate to maintain a substantially round shape to probe 121 when balloon 125 is in a deflated state.

Operation of device 101 is described below according to an exemplary embodiment. A method for toning pelvic floor muscles in a female includes inserting probe 121 into the vagina, pressurizing balloon 125 to inflate balloon 125 such that electrodes 129 contact the walls of the vagina (e.g., to place electrodes 129 snugly against the walls of the vagina to provide an electrical conduction pathway from the electrodes to the muscles and/or associated nerves), and periodically supplying a pulsed electrical stimulation to electrodes 129 to stimulate the muscles. In this manner, balloon 125 allows device 101 to ensure a proper fit with anatomies of different sizes. As the muscles contract in response to the electrical stimulation, the walls of the vagina exert a force on inflated balloon 125, and as the muscles contract, balloon 125 is compressed. Device 101 may include a pressure sensor configured to generate a signal indicative of the contractive force of the muscles on balloon 125 triggered by the electrical stimulation provided through the electrodes 129. The signal from the pressure sensor may be communicated (e.g., via wired or wireless connections) to processing electronics 801. Processing electronics 801 may be configured to process the signal from the pressure sensor to determine information related to muscle contraction caused by the electrical stimulation (e.g., the force or strength of muscle contraction, the duration of muscle contraction, etc.). When muscle contraction stops, the air pressure within balloon 125 causes balloon 125 to expand to original inflated size. The method also includes using a biphasic pulse. The progress of the toning exercises can be monitored by evaluating the increase in strength of muscle activity by measuring muscle contraction over a number of exercise sessions. Toning exercises me be particularly useful for women who have recently given birth. According to one embodiment, device 101 may be used three weeks after childbirth. A method for causing a pleasurable sensation in a user may include similar steps as well as the steps of causing the vibration of clitoral and/or G-Spot stimulators. The pleasurable sensation may be used to cause an orgasm, which in turn causes a release of serotonin and norepinephrine in the user which may improve the user's mood and treat depression, specifically post-partum depression.

According to the exemplary embodiment described, processing electronics 801 supply a biphasic pulse of electrical current to electrodes 129 which in turn stimulates contraction of the muscles. For example, the biphasic pulse may have a first stimulation phase providing a pulse at 12 hertz for 6 seconds followed by a first rest period having a duration of 6 seconds. A second stimulation phase providing a pulse at 25 hertz for six seconds follows the first rest period, and a second rest period having a duration of 6 seconds follows the second phase. The use of a biphasic pulse (e.g., a pulse having two stimulation periods having different frequencies) prevents the muscles from becoming adjusted or de-sensitized to the electrical stimulation. In another embodiment, a multiphasic pulse (e.g., a plurality of different pulse durations and/or frequency between pulses) may be used. This sequence of stimulation phases and rest phases repeats for a treatment period as necessary. A typical treatment period is approximately 15 minutes. In other embodiments, other frequencies and/or durations for the stimulation phases and/or rest periods may be used. For example, in one embodiment, the frequency delivered may be variable, and frequencies up to 50 hertz may be delivered. Within each stimulation phase, a symmetric alternating current may be applied to the muscle via electrodes 129 to reduce the effects of electrophoresis or cataphoresis on the muscle tissues. For example, applying a current of a positive first value for a first pulsewidth (e.g., 200 microseconds), applying no current for 40 microseconds, and then applying a current of a negative first value for a first value (e.g., 200 microseconds) limits the migration of ions with the muscle tissue. This pattern of alternating current pulsewidths may then be repeated at various frequencies (hertz), e.g., 12 hertz, 25 hertz, 50 hertz, etc. Accordingly, the amount of time between the end of the negative current until the beginning of the positive current depends on the frequency. Placing a short rest period (e.g., 40 microseconds) between the bipolar phases may improve circuit reliability.

In the embodiment shown, device 101 may be operated at five different levels of electrical stimulation. In one embodiment, the lowest level of electrical stimulation corresponds to an electrical stimulation current of 10 milliamps, with each subsequent level increasing the electrical stimulation by 10 milliamps such that the second through fifth levels correspond to 20, 30, 40, and 50 milliamps, respectively. In this embodiment, five lamps 178 are illuminated to correspond with the current operating level of the corresponding stimulation element, and the electrical stimulation current is delivered in a series of electrical stimulation phases separated by rest periods as discussed above. According to another embodiment, electronics 801 supply a biphasic pulse of electrical potential between electrodes 129. The electrical potential between electrodes 129 may have five different levels ranging between 10 Volts and 60 Volts. According to another embodiment, stimulation may occur as low as 4-5 Volts. Contraction of the muscle is a function of current (or voltage) amplitude, pulsewidth, and frequency applied to the muscle. Further, the rate at which the muscle relaxes has a minimum persistence time that is affected by the strength and duration of the contraction. If the period (i.e., 1/frequency) of stimulation is greater than the minimum persistence time of the contraction, a user may perceive the stimulation as convulsions rather than a continuous contraction. Accordingly, processing electronics 801 may be configured to control one of frequency, pulsewidth, and amplitude in order to maintain a contraction perceived by the user as substantially continuous. According to one embodiment, processing electronics 801 may be configured to control one of frequency, pulsewidth, and amplitude based on the other two in order to maintain a substantially continuous contraction. Additionally, processing electronics 801 may be configured to ramp at least one of frequency, amplitude, and pulsewidth at the beginning and/or end of each phase. Ramping the frequency, amplitude, and/or pulsewidth may reduce the step function of stimulation entering a phase, which may be uncomfortable or startling for some users. According to one embodiment, the pulsewidth may be stepped up by a fraction of the desired pulsewidth (e.g., 50 microseconds) per cycle until the desired pulsewidth (e.g., 200 microseconds) is reached. Processing electronics 801 may inhibit certain combinations of frequency, current, and voltage. It is believed that these ranges of currents and voltages provide stimulative and toning benefits. In various embodiments, the user, via a control 174 located on a remote control unit, may control the frequency of the electrical signal being supplied, may control the current delivered during each stimulation phase, or may control the voltage delivered during each stimulation phase.

Device 101 may also be operated at multiple, different levels of vibration stimulation intensity. In one embodiment, the user may control the amplitude of vibration generated by the first and second vibrating elements 133, 141 to five different levels, and, in another embodiment, the user may control the frequency of vibration generated by the first and second vibrating elements 133, 141 to five different levels. In this embodiment, indication of vibration level is provided haptically to the user (i.e., the user can feel the level of vibration); however, according to other embodiments, five lamps 178 may be illuminated to correspond with the present operating level of the corresponding vibrating element 133, 141. In the embodiment shown, the first and second vibrating actuators 533, 537 may be controlled independently of each other, and, in this embodiment, interface 115 may include a first pair of vibration control buttons 174 that control vibrations of the first vibrating element 133 and a second pair of vibration control buttons 174 that control the vibration of the second vibrating element 141. In another embodiment, both the first vibrating actuator 533 and the second vibrating actuator 537 are controlled together based upon the vibration level selected by the user by interacting with the vibration control buttons 174.

In the exemplary embodiment described, the level of stimulation and the level of vibration are controllable independently and separately from each other via interaction with the independent stimulation and vibration control buttons 174 as discussed above. In another embodiment, the level of electrical stimulation and the level of vibration are controllable together such that the user can decrease and increase the level of electrical stimulation and the level of vibration together via interaction with a single set of controls.

According to an alternate embodiment, stimulation device 101 may be one component of a stimulation device system that also includes a handheld display device. The handheld display device includes a display screen and a set of display device controls. The handheld display device may be configured to display exciting or erotic material (e.g., videos, pictures, etc.) which may be viewed by the user while using the stimulation device. In one embodiment, the handheld display device may include wireless communication hardware and/or wired communications hardware that allows the material to be downloaded from a source (e.g., the internet, a proprietary server, another local computer, etc.). In one embodiment, the handheld display device may include a local memory device which stores the material to be displayed once it is downloaded. The handheld display device may also be configured to stream the material directly from the source. The user may control the display of the material (e.g., play, pause, rewind, fast-forward, etc.) via the display device controls.

In one embodiment, the handheld display device may be configured to communicate with the processing electronics 801 of the stimulation device via a communication link or connection. In one embodiment, the operation of the stimulation device 101 may be controlled based upon an aspect or property of the material displayed on the display device. In such embodiments, the processing electronics 801 may receive a signal from the handheld display device that provides information related to the aspect of the material being displayed, and the electronic control unit is configured to adjust the level of electrical and/or vibration stimulation based upon the provided information. For example, the level of electrical and/or vibration stimulation delivered by the stimulation device may be altered based on the nature of a scene of the video being displayed.

In another embodiment, the operation of the display device may be controlled based upon operation of the stimulation device 101. In such embodiments, a signal indicative of an operating parameter of the stimulation device 101 may be communicated to the display device, and the operation of the display device may be controlled based upon the operating parameter. For example, in one embodiment, when the stimulation device 101 is powered on, a corresponding signal may be transmitted to the display device causing the display device to power on. As another example, if the stimulation device is on and the display device is on and playing a video, turning the stimulation device off by pressing the power button on the electronic control unit may trigger a signal to be generated to the display device which causes the video to be paused.

Figure 19:
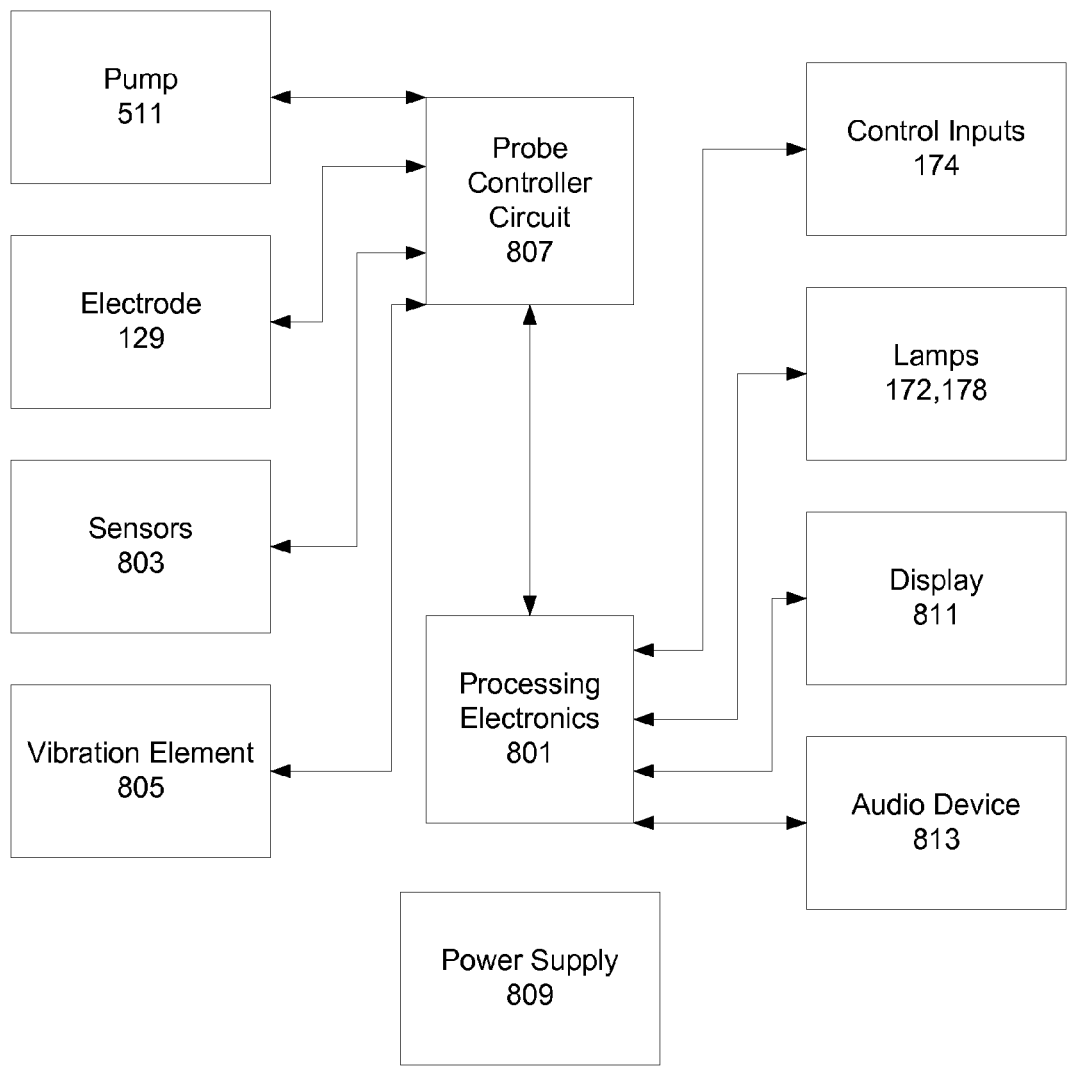
FIG. 19 is a schematic block diagram of the device of FIG. 12, shown according to an exemplary embodiment.

Referring to FIG. 19, a block diagram of device 101 is shown according to an exemplary embodiment. Device 101 is shown to include a pump 511, electrode 129, sensors 803, and vibrating elements 805. Pump 511 is configured to cause inflation of balloon 125 and may be manually operated or motorized. First electrode 129a and/or second electrode 129b are configured to provide an electrical signal (e.g., current, voltage, frequency, etc.) to a muscle in communication with the electrode. According to various embodiments, device 101 may have one or a plurality of electrodes 129 and may include one or more sensors 803 (e.g., a capacitive sensor, a pressure sensor, a conductivity sensor, etc.). Sensors 803 may be disposed in any suitable location in device 101 (e.g., in handle 111, in cavity 503 under G-Spot stimulator 133, etc.). Vibrating elements 805 (e.g., G-Spot stimulator 133, clitoral stimulator 141, actuation motors 533, 537, etc.) may each have a vibrating motor or may share a vibrating motor, and may be configured to provide a pleasurable sensation to a user or to provide haptic feedback to a user, the haptic feedback being in response to user input through controls 174 or as an indication that balloon 125 has been inflated to a predetermined pressure. The pleasurable sensation may induce a user to maintain compliance with an exercise regimen.

According to an exemplary embodiment, device 101 is shown to include control inputs 174, lamps 178, 172, display 811, audio device 813, processing electronics 801, probe controller circuit 807, and power supply 809. The control inputs may include any suitable user interface, e.g., buttons 174, toggles, switches, an electro-acoustic transducer configured to receive voice commands, a touch sensitive display, etc. Lamps such as lamps 178, 172 may provide information to a user through illumination, brightness, color, blinking pattern, and/or illumination of a subset of a plurality of spatially oriented lamps. Display 811 may also be configured to provide alphanumeric or graphical images and may include a touchscreen (e.g., touch sensitive surface), the touchscreen being configured to both provide information to a user and to receive input from a user. Using a touchscreen would provide an easy to clean surface, thereby facilitating sanitary hygiene. Audio device 813 may be a speaker configured to provide aural information to a user and may be combined with or separate from the electro-acoustic transducer control input. Audio device 813 may be configured to provide motivation and/or audio instruction to a user, to announce that the pressure inside balloon 125 has reached a predetermined level, or to request a user to manually force a contraction of the muscle in communication with electrodes 129. Probe controller circuit 807 may include any number of mechanical or electrical circuitry components or modules for a pump 511, electrode 129, sensors 803, and/or vibrating elements 805 of device 101. For example, circuit 807 may be configured to send electrical signals to pelvic floor muscles while sending response information to processing electronics 801.

Device 101 is further shown to include a power supply 809. Power supply 809 is configured to provide electrical power to device 101 and components thereof. According to an exemplary embodiment, device 101 is configured to be powered by a 6 Volt source (e.g. four AA batteries located in shaft 211 or a 6-Volt battery). According to other embodiments, device 101 may use other voltages, a rechargeable battery, or may be plugged into utility power supply. Power supply 809 or processing electronics 801 may be configured to increase the voltage and/or amperage available to electrodes 129. According to one embodiment, the maximum electrical potential generated between the first electrode 129a and second electrode 129b is approximately 80 Volts. According to another embodiment, it is believed that the maximum therapeutic range of the electrical potential generated between first electrode 129a and second electrode 129b is approximately 50 Volts. According to the exemplary embodiment, power supply 809 and/or processing electronics 801 are configured to provide power to 3-Volt motors used in vibrating elements 805.

Figure 20:
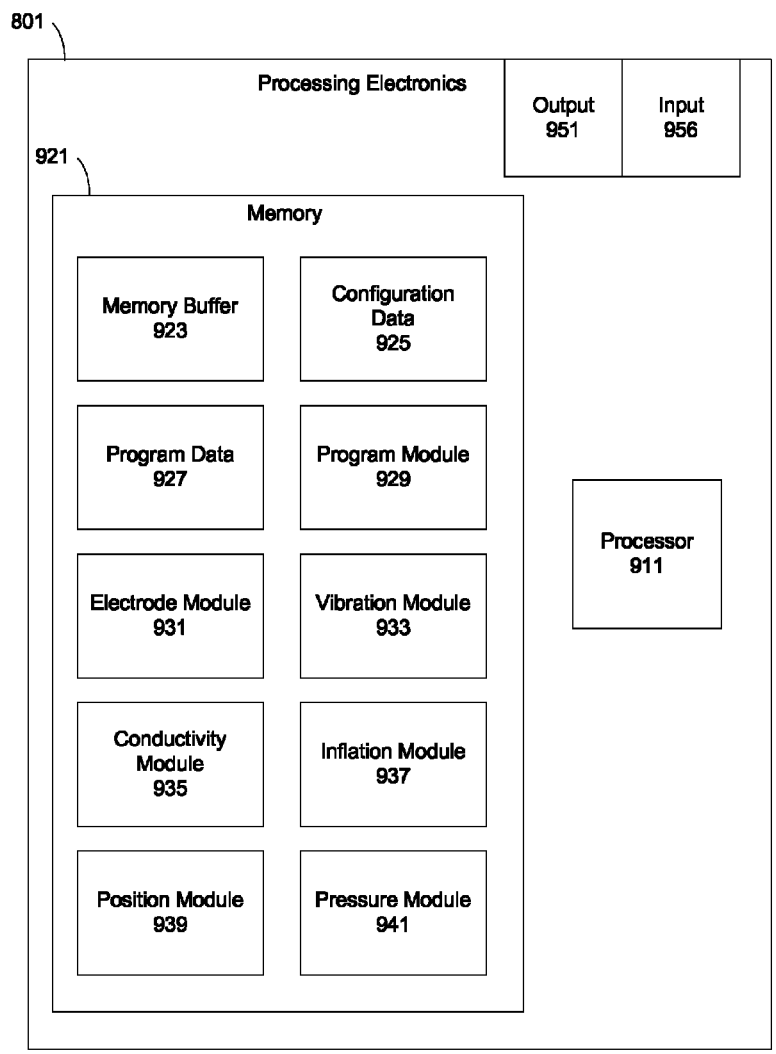
FIG. 20 is a schematic block diagram of the processing electronics of the device of FIG. 12, shown according to an exemplary embodiment.

Referring to FIG. 20, a detailed block diagram of processing electronics 801 of FIG. 19 is shown, according to an exemplary embodiment. Processing electronics 801 includes a processor 911 and a memory 921. According to an exemplary embodiment, processor 911 is configured to execute computer code stored in memory 921 to complete and facilitate the activities described herein. For example, memory 921 is shown to include modules 923-941 which are computer code modules (e.g., executable code, object code, source code, script code, machine code, etc.) configured for execution by processor 911. When executed by processor 911, processing electronics 801 is configured to complete the activities described herein. Processing electronics includes hardware circuitry for supporting the execution of the computer code of modules 923-941. For example, processing electronics 801 includes hardware interfaces (e.g., output 951) for communicating control signals (e.g., analog, digital) from processing electronics 801 to circuit 807. Processing electronics 801 may also include an input 956 for receiving, for example, sensor data from circuit 807, response information from circuit 807, user inputs from control inputs 174, or for receiving data or signals from other systems or devices. According to various embodiments, processor 911 may be or include one or more microprocessors, an application specific integrated circuit (ASIC), a circuit containing one or more processing components, a group of distributed processing components, circuitry for supporting a microprocessor, or other hardware configured for processing. Memory 921 can be any volatile or non-volatile memory device capable of storing data or computer code relating to the activities described herein.

Memory 921 includes a memory buffer 923 for receiving sensor data, for example response information, pressure data, voltage data, capacitive sensing data, conductivity data, etc. The sensor data may be stored in memory buffer 923 until buffer 923 is accessed for data. For example, a program module 929, electrode module 931, vibration 933, conductivity module 935, inflation module 937, position module 939, pressure module 941, or another process that uses sensor data may access buffer 923. The sensor data stored in memory 921 may be stored according to a variety of schemes or formats. For example, the sensor data may be stored as streaming data, peak values, synchronous, asynchronous, separate buffers for each data type, one buffer for all sensor data, or any other suitable format for storing sensor information.

Memory 921 further includes configuration data 925. Configuration data 925 includes data relating to device 101, such as electrode information that the electrode module 931 can interpret to determine how to command the electrodes 129 to cause a muscle contraction, for example the number of electrodes, electrode conductivity, conductivity as a function of expansion or pressure, etc. According to another embodiment, configuration data 925 may include pump information, such as whether the pump 511 is hand-operated or motorized, and control information of the motorized pump. According to another embodiment, configuration data 925 may include sensor information, such as the existence, location, and calibration of pressure sensors, conductivity sensors, capacitive sensors, and the like. According to another embodiment, configuration data 925 may include response information configuration data which program module 929 can interpret to determine if the response information will include an electrical signal received from at least one of the electrodes 129, a pressure signal received from a pressure sensor, or both.

Memory 921 further includes a program data 927 which includes data relating to the toning program or stimulation program. Program data 927 may include data that program module 929 can interpret to determine how to command the electrical signal sent to electrodes 129. For example, program data 927 may include electrical stimulation data including data relating to current, voltage, frequency, number of phases of stimulation signal, duration and pattern of stimulation periods, and/or duration and pattern of rest periods. Program data 927 may include vibrational stimulation data including data relating to vibration, frequency, pattern, etc. Program data 927 may be stored in memory 921 by the user or another, may be downloaded into memory 921, and may be synchronized with audio or video files.

Memory 921 further includes a program module 929 which includes logic for using configuration data 925, program data 927, sensor data from the memory buffer 923, and/or data received from another module to carry out the pleasurable sensations or muscle toning program, e.g., providing stimulation commands to electrode module 931 or vibration module 933. Program module 929 may output data to a data logging module for recording, may cause outputs for providing an indication to a user, and may cause an output requesting a user to perform an activity (e.g., inserting probe 121, pressurizing balloon 125, forcing a contraction, etc.). Program module 929 may include logic to cause closed-loop control of the electrical stimulation and/or vibrational stimulation based on response information received from memory buffer 923, electrode module 931, conductivity module 935, and/or pressure module 941.

Memory 921 further includes an electrode module 931 which includes logic for causing a contraction of a muscle in communication with electrode 129. Electrode module 931 may control the stimulation of a muscle in communication with electrodes 129 based on conductivity information received from conductivity module 935, position information received from position module 939, and/or pressure information received from pressure module 941. Electrode module 931 may include logic to control the current or voltage provided by electrodes 129 as a function of frequency, or to control the frequency in response to the current or voltage. According to the exemplary embodiment, electrode module 931 may be configured to operate at five levels of stimulation, which may be indicated to a user using the five lamps 178 shown on interface 115. According to an alternate embodiment, electrode module 931 may include logic to use an 8-bit register to control the frequency, current, or voltage of the stimulation. Using an 8-bit register provides fine resolution for precise stimulation effects and toning.

Memory 921 further includes a vibration module 933 which includes logic for causing a vibrating element to vibrate. Vibration module 933 may include logic for actuating G-Spot vibration actuator 533, clitoral vibration actuator 537, and a haptic feedback motor. For example, actuators 533 and 537 may be actuated dependently or independently and may be actuated in response to user input through controls 174, in response to response information, or synchronized with music or video. Vibration module 933 may operate actuators 533 and 537 at five different levels of vibration. Vibration module 933 may receive data from memory buffer 923, program data 927, and program module 929.

Memory 921 is shown to include a conductivity module 935 which includes logic for determining the conductivity of the environment of probe 121, balloon 125, and/or electrodes 129. Conductivity of the environment is dependent on many factors. For example, conductivity may depend on the conductivity and quantity of artificial lubricants used, the quantity of vaginal fluid present, which may change from day to day or during use, and/or the expansion of electrodes 129. A conductivity sensor in probe 121 may measure the resistivity between electrodes 129 or measure the current delivered for a provided voltage. According to one embodiment, a low voltage (e.g., 2 Volts) may be provided across electrodes 129, the resulting current is measured, and resistance is calculated. The low voltage may be provided before beginning a toning or exercise program or may be provided during a portion of a rest period (e.g., between phases). Conductivity module 935 may receive sensor data directly or through memory buffer 923. Conductivity module 935 may provide conductivity information to electrode module 931 or any other module requiring conductivity information.

Memory 921 is shown to include an inflation module 937 which includes logic for providing an indication to a user that the pressure inside balloon 125 has reached a predetermined value. According to one embodiment, the predetermined value is a pressure stored in program data 927. Inflation module 937 may use sensor data from memory buffer 923 or pressure information from pressure module 941. Inflation module 937 may include logic for causing inflation of balloon 125. For example, inflation module 937 may cause a request for a user to actuate pump 511 or may cause actuation of a motorized pump 511. Inflation module 937 may control pump 511 using configuration data 925 and pressure data received from memory buffer 923 or pressure module 941.

Memory 921 is shown to include a position module 939 which includes logic for determining if probe 121 is inserted and/or properly positioned. According to one embodiment, position module 939 may receive capacitive sensor data from memory buffer 923. According to an alternative embodiment, position module 939 may determine insertion of probe 121 from a change in continuity or a change in resistance between electrodes 129. According to another alternative embodiment, position module 939 may request user confirmation that probe 121 and/or balloon 125 are inserted, for example, by providing input via control inputs 174 on controller 104. Position module 939 may cause output from electrode module 931 to be inhibited if position module 939 determines that balloon 125 has been removed from the vagina. For example, position module 939 may cause electrodes 129 to stop providing an electric signal, or position module 939 may provide position information to program module 929 or to electrode module 931.

Memory 921 further includes a pressure module 941 which includes logic for determining the pressure inside balloon 125. Pressure module 941 may use configuration data 925, pressure data received directly from the pressure sensor, or pressure data received from memory buffer 923. Pressure module 941 may provide pressure information to inflation module 937 and program module 929. Pressure module 941 may provide pressure information to electrode module 931, or may inhibit processing electronics 801 from causing a contraction of the muscle if the pressure in balloon 125 is below a threshold value, e.g., balloon 125 has not been sufficiently inflated. Pressure module 941 may receive response information from the pressure sensor.

Figure 21:
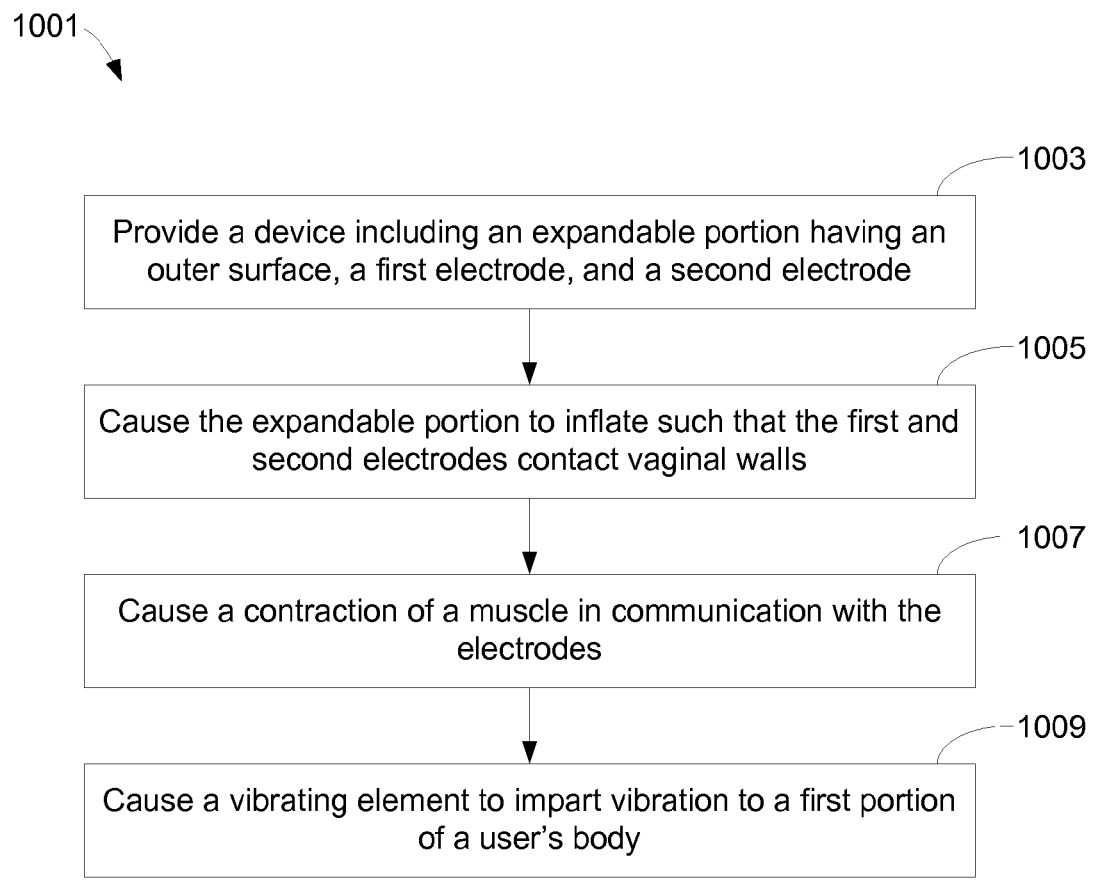
FIG. 21 is a schematic flow chart of a process for toning pelvic floor muscles, shown according to an exemplary embodiment.

Referring to FIG. 21, a flowchart of a process 1001 for toning pelvic floor muscles is shown according to an exemplary embodiment. Process 1001 is shown to include the steps of providing a device as described above and including an expandable portion having an outer surface, a first electrode, and a second electrode (step 1003). Process 1001 further includes the steps of causing the expandable portion to inflate such that the first and second electrodes contact vaginal walls (step 1003), and causing a contraction of the muscle in communication with the electrodes (step 1007). Process 1001 further includes causing a vibrating element to impart vibration to a first portion of a user's body (step 1009). According to one embodiment, the first and second electrodes couple to the outer surface of the expandable portion and are configured to cause a contraction of a muscle and communication with the electrodes. According to alternate embodiments, process 1001 may include additional or fewer steps. For example, process 1001 may include inserting the expandable portion in a vaginal cavity, deflating the expandable portion, and removing the probe from the vaginal cavity and may not include causing a vibrating element to impart vibration (step 1009).

Figure 22:
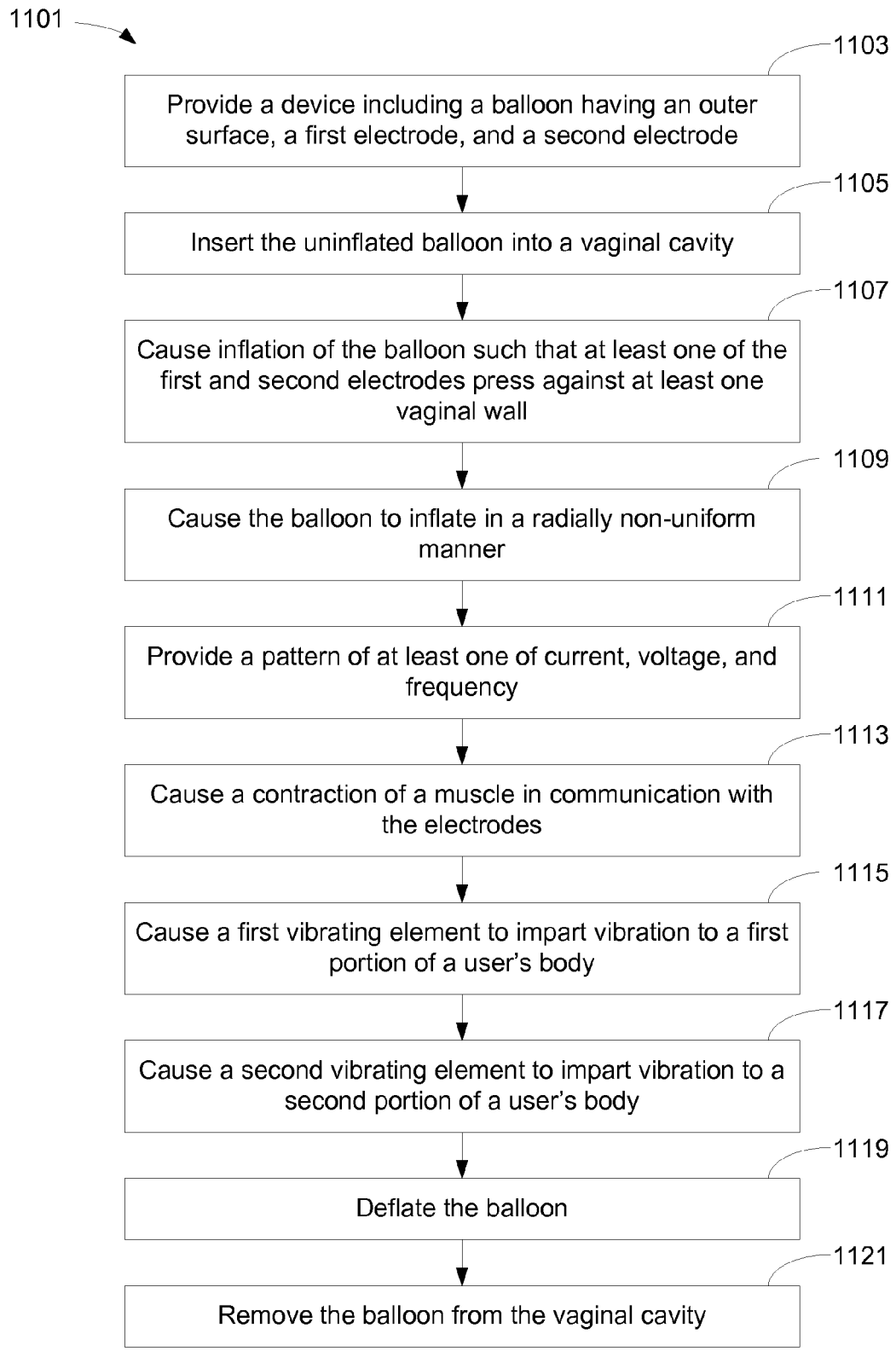
FIG. 22 is a schematic flow chart of a process for toning pelvic floor muscles, shown according to another exemplary embodiment.

Referring to FIG. 22, a flowchart of process 1101 for toning pelvic floor muscles is shown according to an exemplary embodiment. Process 1101 is shown to include the steps of providing a device as described above and including a balloon having an outer surface, a first electrode, and a second electrode (step 1103) and inserting the balloon into a vaginal cavity (step 1105). Process 1101 further includes the steps of causing inflation of the balloon such that at least one of the first and second electrodes press against at least one vaginal wall (step 1107) and causing the balloon to inflate in a radially non-uniform manner (step 1109).

According to various embodiments, step 1107 may include requesting a user to actuate pump 511, causing actuation of pump 511, and/or causing operation of a motorized pump. Step 1109 may include unfolding of bellows or non-uniform expansion of balloon portions having different thicknesses. Process 1101 is shown to include the steps of providing a pattern of at least one of current, voltage, and frequency (step 1111), causing a contraction of a muscle in communication with the electrodes (step 1113), causing a first vibrating element to impart vibration to a first portion of a user's body (step 1115), and causing a second vibrating element to impart vibration to a second portion of a user's body (step 1117). Providing the pattern in step 1111 may or may not cause the contraction or vibrations in steps 1113-1117, and the contraction and vibrations in steps 1113-1117 may be caused by the same or different electrical signals. Causing a contraction of a muscle in step 1113 may be through electrical stimulation via electrodes 129 or may be requesting a user to manually or volitionally force a contraction of the muscle. The balloon may then be deflated (step 1119) and removed from the vaginal cavity (step 1121).

Various alternate embodiments of the process described are contemplated. For example, the order of steps may be changed, e.g., causing a contraction of a muscle (step 1113), causing a first vibrating element to impart vibration (step 1115), and causing a second vibrating element to impart vibration (1117) may occur in any order, may occur simultaneously, or may occur repeatedly. Process 1101 may not include all of the steps listed, e.g., not include causing first or second vibrating elements to impart vibration (steps 1115 and 1117). Process 1101 may include additional steps, e.g., lubricating the balloon or requesting insertion of the balloon into a vaginal cavity, for example, by indicating that device 101 is initialized and ready for insertion (e.g., illuminating in indicator lamp 172), providing an aural request through speaker audio device 813, or providing instructions along with providing device 101.

It is also important to note that the construction and arrangement of the elements of the devices as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims. Any means-plus-function clause is intended to cover the structures described herein as performing the recited function and not only structural equivalents but also equivalent structures.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Other substitutions, modifications, changes and omissions may be made in the design, operating configuration, and arrangement of the preferred and other exemplary embodiments without departing from the spirit of the appended claims.

What is claimed is:

1. An apparatus for the treatment of urinary incontinence comprising:
   a shaft;
   a balloon surrounding at least a portion of the shaft and configured for movement between an inflated state and a deflated state;
   a first electrode coupled to a first portion of an outer surface of the balloon, the first electrode configured to cause a contraction of at least one muscle in communication with the first electrode;
   a second portion of outer surface of the balloon having a longitudinal fold having a thickness less than the first portion of the balloon and separating the first portion from a third portion of the outer surface of the balloon along a longitudinal axis of the shaft, the second portion being exposed to an exterior of the apparatus when the balloon is in the deflated state; and
   a second electrode coupled to the third portion;
   wherein the balloon is configured to inflate in a radially non-uniform manner in response to the difference in thicknesses of the first portion and the second portion.

2. The apparatus of claim 1 comprising a pump in communication with the balloon and configured to cause inflation of the balloon such that at least one of the first and second electrodes press against a vaginal wall of a user.

3. The apparatus of claim 1 comprising processing electronics configured to inhibit at least one of the first and second electrodes from causing a contraction of the at least one muscle in communication with the at least one of the first and second electrodes until the balloon has been inflated to a predetermined pressure.

4. The apparatus of claim 1 comprising processing electronics configured to cause an indication in response to a determination that a pressure inside the balloon has reached a predetermined value.

5. The apparatus of claim 1 comprising processing electronics configured to cause an indication in response to a determination that the balloon has been inflated to a pressure equal to or greater than a predetermined value.

6. The apparatus of claim 1 comprising processing electronics configured to cause inflation of the balloon.

7. The apparatus of claim 1 comprising processing electronics configured to cause a current of between 10 milliamps and 50 milliamps.

8. The apparatus of claim 1 comprising processing electronics configured to cause an electric potential difference between the first electrode and the second electrode.

9. The apparatus of claim 8, wherein the electric potential difference is between 0 and 80 Volts.

10. The apparatus of claim 8, wherein the electric potential difference is between 10 Volts and 50 Volts.

11. The apparatus of claim 8, wherein the processing electronics are configured to control the electric potential difference.

12. A stimulation device for creating a pleasurable sensation in a user comprising:
    an expandable portion configured to assume a plurality of states of expansion between minimum expansion and maximum expansion;
    a vibrating element spaced from an outer surface of the expandable portion; and
    an electrode coupled to the outer surface of the expandable portion, the electrode configured to transmit electrical current to a muscle in communication with the electrode to cause a contraction of the muscle;
    the expandable portion comprising a first portion and a second portion, the first and second portions separated by a longitudinal fold, the electrode coupled to the first portion and the vibrating element adjacent to one of the first and second portions, wherein the longitudinal fold is exposed to an exterior of the stimulation device when in a non-expanded state.

13. The device of claim 12 comprising
    processing electronics configured to cause an electrical signal in the electrode and to control an aspect of vibration of the vibrating element, wherein the electrode is coupled to a top surface of the outer surface of the expandable portion.

14. The device of claim 12, wherein the vibrating element is configured to impart vibration to a first portion of the user's body.

15. The device of claim 12 comprising a second vibrating element configured to impart vibration to a second portion of the user's body.

16. The device of claim 12, wherein the expandable portion is configured to be inserted into a vagina.

17. The device of claim 12 comprising a pump in communication with the expandable portion and configured to cause inflation of the expandable portion.

18. The device of claim 13, wherein the electrode is formed of an expandable material.

19. The device of claim 18, wherein the expandable material is an electrically conductive silicone rubber.

20. A stimulation device for creating a pleasurable sensation in a user comprising:
- a shaft having a proximal end and a distal end, the proximal end being interconnected to a housing;
- an operative portion located between the proximal end and the distal end and configured to be located within at least one of a vagina, an anal canal, and a rectum when the device is in an inserted position;
- only one balloon circumferentially surrounding the operative portion of the shaft, the balloon comprising first and second surfaces separated by a longitudinal fold; and
- a first electrode and a second electrode, the first and second electrodes disposed on the first and second surfaces, respectively, of the balloon and configured to cause a contraction of a muscle in communication with the first and second electrodes;
- wherein the balloon is configured to inflate such that the first and second electrodes press against at least one wall of the at least one of a vagina, an anal canal, and a rectum.

* * * * *